United States Patent
Chen et al.

(10) Patent No.: US 12,016,724 B2
(45) Date of Patent: Jun. 25, 2024

(54) AUTOMATIC CLOSED-LOOP ULTRASOUND PLANE STEERING FOR TARGET LOCALIZATION IN ULTRASOUND IMAGING AND ASSOCIATED DEVICES, SYSTEMS, AND METHODS

(71) Applicant: KONINKLIJKE PHILIPS N.V., Eindhoven (NL)

(72) Inventors: Alvin Chen, Cambridge, MA (US); Cosmas Mwikirize, Eindhoven (NL); Mingxin Zheng, Cambridge, MA (US); Kunal Vaidya, Boston, MA (US); Shyam Bharat, Arlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/762,209

(22) PCT Filed: Sep. 10, 2020

(86) PCT No.: PCT/EP2020/075308
§ 371 (c)(1),
(2) Date: Mar. 21, 2022

(87) PCT Pub. No.: WO2021/058288
PCT Pub. Date: Apr. 1, 2021

(65) Prior Publication Data
US 2022/0370034 A1  Nov. 24, 2022

Related U.S. Application Data

(60) Provisional application No. 62/906,368, filed on Sep. 26, 2019.

(51) Int. Cl.
*A61B 8/08*  (2006.01)
*A61B 8/00*  (2006.01)

(52) U.S. Cl.
CPC ............ *A61B 8/0841* (2013.01); *A61B 8/085* (2013.01); *A61B 8/0883* (2013.01); *A61B 8/0891* (2013.01)

(58) Field of Classification Search
CPC ..... A61B 8/0841; A61B 8/085; A61B 8/0883; A61B 8/0891; A61B 8/12; A61B 8/46;
(Continued)

(56) References Cited

U.S. PATENT DOCUMENTS 6,443,896 B1  9/2002  Detmer
6,733,458 B1  5/2004  Steins et al.
(Continued)

FOREIGN PATENT DOCUMENTS

WO  2004086082 A1  10/2004
WO  2006109219 A1  10/2006
(Continued)

OTHER PUBLICATIONS

International Search Report and Written Opinion for PCT/EP2020/075308; dated Dec. 15, 2020; 14 pages.
(Continued)

*Primary Examiner* — Boniface N Nganga

(57) ABSTRACT

Ultrasound image devices, systems, and methods are provided. An ultrasound imaging system comprising a processor circuit configured to receive, from an ultrasound transducer array, a plurality of images of a patient body at different imaging planes; determine a first imaging plane based on a first image of the plurality of images by applying a first predictive network, wherein a second image of the plurality of images is based on the first imaging plane, and wherein the second image includes an imaging view of at least one of an anatomy of the patient body or a medical device within the anatomy; apply a second predictive network to the second image to generate segmentation data; and
(Continued)

output, to a display, a displayed image including an indication of a first portion of the at least one of the anatomy or the medical device based on the segmentation data.

18 Claims, 12 Drawing Sheets

(58) Field of Classification Search
CPC ......... A61B 8/569; A61B 8/463; A61B 8/483;
A61B 8/488; A61B 8/585; A61B 8/5215;
A61B 8/54; G06N 3/045; G06N 3/084;
G06N 3/048; G06N 3/08; G06T 7/11;
G06T 2207/10136; G06T 2207/20104
See application file for complete search history.

(56) References Cited

U.S. PATENT DOCUMENTS

| | | | |
|---|---|---|---|
| 2003/0120150 | A1 | 6/2003 | Govari |
| 2004/0193042 | A1 | 9/2004 | Scampini et al. |
| 2005/0228280 | A1 | 10/2005 | Ustuner et al. |
| 2012/0069347 | A1 | 3/2012 | Klein et al. |
| 2012/0253181 | A1 | 10/2012 | Okamura et al. |
| 2014/0013849 | A1 | 1/2014 | Gerard et al. |
| 2014/0187942 | A1 | 7/2014 | Wang et al. |
| 2015/0011886 | A1* | 1/2015 | Radulescu ............... A61B 8/12 600/447 |
| 2015/0272549 | A1 | 10/2015 | Samset et al. |
| 2016/0317118 | A1* | 11/2016 | Parthasarathy ........... G06T 7/70 |
| 2016/0367322 | A1 | 12/2016 | Jain et al. |
| 2017/0360412 | A1* | 12/2017 | Rothberg ............. G06T 19/006 |
| 2018/0125460 | A1* | 5/2018 | Perrey .................... A61B 8/523 |
| 2019/0336108 | A1* | 11/2019 | Hope Simpson ... G01S 15/8915 |
| 2020/0027237 | A1* | 1/2020 | Baumgartner ......... G06V 10/82 |
| 2020/0069285 | A1* | 3/2020 | Annangi ............... A61B 8/4254 |
| 2020/0196984 | A1* | 6/2020 | Sprung ...................... G06T 7/10 |
| 2021/0000553 | A1* | 1/2021 | St. Pierre ............... G06N 20/00 |
| 2022/0198669 | A1* | 6/2022 | Chen .................... G06T 7/0016 |

FOREIGN PATENT DOCUMENTS

| | | |
|---|---|---|
| WO | 2015101949 A1 | 7/2015 |
| WO | 2019175129 A1 | 9/2019 |
| WO | 2020201183 A1 | 10/2020 |
| WO | 2021028416 A1 | 2/2021 |
| WO | 2021028467 A1 | 2/2021 |

OTHER PUBLICATIONS

Pourtaherian A. et al., "Robust and semantic needle detection in 3D ultrasound using orthogonal-plane convolutional neural networks", Int J Comput Assist Radiol Surgery, 2018; vol. 13, No. 9, pp. 1321-1333.

Baumgartner C.F. et al., "Real-Time Standard Scan Plane Detection and Localisation in Fetal Ultrasound Using Fully Convolutional Neural Networks"Medical Image Computing and Computer-Assisted Intervention—MICCAI 2016, 9 pages.

Milletari, F. et al., "Straight to the point: reinforcement learning for user guidance in ultrasound", arXiv:1903.00586v1, 2019, 11 pages.

Prevost, R. et al., "3D freehand ultrasound without external tracking using deep learning", Medical Image Analysis, 2018, vol. 48, pp. 187-202.

Mwikirize C. et al., "Learning needle tip localization from digital subtraction in 2D ultrasound", Int J Comput Assist Radiol Surg, 2019, vol. 6, pp. 1017-1026.

Mwikirize C. et al., "Convolution neural networks for real-time needle detection and localization in 2D ultrasound", Int J Comput Assist Radiol Surg. 2018, vol. 13, No. 5, pp. 647-657.

Ren, S. et al., "Faster R-CNN: Towards Real-Time Object Detection with Region Proposal Networks", IEEE Tieee Trans. Pattern Anal. Mach. Intell, 2017, vol. 39, No. 6, pp. 1137-1149.

Ronneberger, O. et al., "U-Net: Convolutional Networks for Biomedical Image Segmentation", arXiv:1505.04597v1, 8 bages.

Khanal et al., "EchoFusion: Tracking and Reconstruction of Objects in 4D Freehand Ultrasound Imaging without External Trackers"; Lecture Notes in Computer Science 2018, vol. 11076, pp. 117-127.

Chen et al: "Combining Fully Convolutional and Recurrent Neural Networks For 3d Biomedical Image Segmentation"; 30th Conference on Neural Information Processing Systems (Nips 2016), Barcelona, Spain, pp. 3044-3052.

Milletari et al: "V-Net: Fully Convolutional Neural Networks For Volumetric Medical Image Segmentation"; Arxiv:1606.04797v1, Jun. 15, 2016, 11 Pages.

Valipour et al: "Recurrent Fully Convolutional Networks For Video Segmentation", IEEE Winter Conference on Applications of Computer Vision (WACV), 2017, pp. 29-36.

Yang et al: "Fine-Grained Recurrent Neural Networks For Automatic Prostate Segmentation in Ultrasound Images"; 2017, Association for the Advancement of Artificial Intelligence, 8 pages.

* cited by examiner

AUTOMATIC CLOSED-LOOP ULTRASOUND PLANE STEERING FOR TARGET LOCALIZATION IN ULTRASOUND IMAGING AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2020/075308, filed on Sep. 10, 2020, which claims the benefit U.S. Provisional Patent Application No. 62/906,368, filed on Sep. 26, 2019. These applications are hereby incorporated by reference herein.

TECHNICAL FIELD

The present disclosure relates generally to ultrasound imaging and, in particular, to providing automatic closed-loop ultrasound plane steering for localization of target anatomical structure and/or medical device.

BACKGROUND

Ultrasound can provide non-radiated, safe, and real-time, dynamic imaging of anatomy and/or medical devices during medical procedures (e.g., diagnostics, interventions, and/or treatments). In recent years, minimally invasive endovascular methods have been introduced to treat diseases such as peripheral vascular disease (PVD), cardiovascular disease (CVD), and structural heart disease (SEM), usually under image guidance. In particular, three-dimensional (3D) ultrasound imaging can provide visualization of soft tissue structures and medical devices and/or interventional devices moving through complex anatomy. Additionally, ultrasound imaging can provide view guidance to facilitate percutaneous procedures, such as biopsies, vascular access, regional anesthesia delivery, and emergency monitoring. All of these clinical scenarios involve the navigation of devices, such as needles, guide wires, catheters, intravascular ultrasound devices, therapeutic devices, implantable devices such as mitral clips, and many others, through a patient's body under ultrasound imaging. Similarly, some clinical procedures may require visualization of anatomical structures and views, such as blood vessels, mitral leaflets, canonical cardiac views, or specific abdominal views, under ultrasound imaging.

However, 3D volume acquisition comes at a cost of reduced spatiotemporal resolution. Furthermore, when the objects (e.g., anatomical structures or medical devices) of interest have a small size and/or a thin geometry (e.g., as in the examples discussed above), the small-sized and/or the thinly-shaped objects may appear in only a fraction of the total voxel count within the 3D ultrasound volume, and thus can be easily missed. Visualization of small-sized and/or the thinly-shaped structures can be challenging in 3D ultrasound given the reduced spatiotemporal resolution.

SUMMARY

There remains a clinical need for improved systems and techniques for providing imaging guidance and target localization. Embodiments of the present disclosure provide techniques to efficiently localize objects of interest by utilizing an automatic closed-loop deep learning-based ultrasound imaging plane steering framework. The objects of interest may be thin moving objects (e.g., a needle, a guidewire, a catheter, or a guide catheter) or complex anatomical structures. The framework includes a series of deep learning-based prediction networks that operate on two-dimensional (2D) ultrasound images, X-plane images, and/or multiplane images acquired by a three-dimensional (3D) imaging probe. The series of prediction networks are trained to perform device recognition, device tracking, and device segmentation and tip localization. Each prediction network provides a prediction of an ultrasound imaging plane for steering the 3D probe (e.g., in the form of elevation angles and/or beam indices) towards a target or optimal imaging plane. The series of prediction networks are configured in a pipeline configuration, where the output of one prediction network is used to initialize a next prediction network in the series. In an example, an image may be cropped based on a prediction obtained from one prediction network and the cropped image may be fed into a next prediction network in the series. The closed-loop form is achieved by iterating between prediction outputs and physically controlling or steering the 3D imaging probe, for example, via electronic steering mechanisms.

To enable real-time imaging view guidance, the framework searches for the medical device and/or localizes a certain portion (e.g., a tip) of the medical device using a coarse-to-fine resolution scales. For example, the framework may perform the search within a volumetric field-of-view (FOV) from a coarse spatial resolution scale to a fine spatial resolution scale. Additionally or alternatively, the framework may perform the search from a low imaging resolution scale to a higher imaging resolution scale. In an embodiment, the series of prediction networks may include a first prediction network trained to identify a medical device at a coarse resolution scale, a second prediction network trained to track the medical device at a fine resolution scale, and a third prediction network trained to perform segmentation and tip localization in order. The output of the third prediction network may be output to a display, where an output image may include indicators and/or markings indicating the tip and/or the medical device in the output image.

In one embodiment, an ultrasound imaging system comprising a processor circuit in communication with an ultrasound transducer array, the processor circuit configured to receive, from the ultrasound transducer array, a first image of a patient body; determine a first imaging plane configuration based on the first image by applying a first predictive network associated with image identification to the first image; receive, from the ultrasound transducer array, a second image of the patient body based on the first imaging plane configuration, wherein the second image includes an imaging view of at least one of an anatomy of the patient body or a medical device within the anatomy; apply a second predictive network associated with image segmentation to the second image to generate segmentation data; and output, to a display in communication with the processor circuit, a displayed image including an indication of a first portion of the at least one of the anatomy or the medical device based on the segmentation data.

In some embodiments, wherein the processor circuit is configured to receive, from the ultrasound transducer array, a third image based on the first imaging plane configuration; and determine a second imaging plane configuration based on the third image, wherein the second image is further received based on the second imaging plane configuration. In some embodiments, wherein the first imaging plane configuration includes a first parameter associated with a first beam steering angle, and wherein the second imaging plane configuration includes a second parameter associated with a second beam steering angle less than the first beam steering angle. In some embodiments, wherein the first imaging plane configuration includes a first parameter associated with a first imaging resolution, and wherein the second imaging plane configuration includes a second parameter associated with a second imaging resolution higher than the first imaging resolution. In some embodiments, wherein the processor circuit configured to determine the second imaging plane configuration is further configured to apply a third predictive network associated with image identification to the third image to generate a second imaging plane configuration, the third predictive network being different from the first predictive network. In some embodiments, wherein the first predictive network includes a convolutional encoder trained to identify the at least one of the anatomy or the medical device based on a first spatial resolution; and the third predictive network includes a convolutional encoder trained to determine a distance metric associated with an in-plane imaging view of the at least one of the anatomy or the medical device at a second spatial resolution finer than the first spatial resolution. In some embodiments, wherein the first predictive network includes a convolutional encoder trained to identify the at least one of the anatomy or the medical device based on a first image resolution; and the third predictive network includes a convolutional encoder trained to determine a distance associated with an in-plane imaging view of the at least one of the anatomy or the medical device based on a second image resolution higher than the first image resolution. In some embodiments, wherein the processor circuit configured to receive, from the ultrasound transducer array, a sequence of images of the patient body, the sequence of images including the first image, and wherein each image of the sequence of images is based on a different imaging plane configuration; determine the first imaging plane configuration is further configured to apply the first predictive network to each image of the sequence of images to generate a confidence level associated with a presence of the at least one of the anatomy or the medical device in the image; and select the first imaging plane configuration based on the confidence level. In some embodiments, wherein the sequence of images includes at least a short-axis image and a long axis-image. In some embodiments, wherein the processor circuit is further configured to determine a third imaging plane configuration based on the segmentation data, the third imaging plane configuration includes a parameter associated with at least one of beam steering angle, a signal gain, or an imaging depth of focus; and the displayed image is further based on the third imaging plane configuration. In some embodiments, wherein the second image includes the medical device comprising at least one of a needle, a guidewire, a catheter, or a guide catheter. In some embodiments, wherein the ultrasound transducer array is a two-dimensional (2D) ultrasound transducer array. In some embodiments, the system further comprises an electronic steering controller in communication with the ultrasound transducer array and the processor circuit, wherein the processor circuit is configured to transmit, to the electronic steering controller, an instruction to configure the ultrasound transducer array based on the first imaging plane configuration.

In one embodiment, a method of ultrasound imaging, comprising receiving, at a processor circuit in communication with an ultrasound transducer array, a first image of a patient body; determining a first imaging plane configuration based on the first image by applying a first predictive network associated with image identification to the first image; receiving, from the ultrasound transducer array, a second image of the patient body based on the first imaging plane configuration, wherein the second image includes an imaging view of at least one of an anatomy of the patient body or a medical device within the anatomy; applying a second predictive network associated with image segmentation to the second image to generate segmentation data; and outputting, to a display in communication with the processor circuit, a displayed image including an indication of a first portion of the at least one of the anatomy or the medical device based on the segmentation data.

In some embodiments, the method further comprises receiving, from the ultrasound transducer array, a third image of the patient body based on the first imaging plane configuration; determining a second imaging plane configuration based on the third image, and wherein the second image is further received based on the second imaging plane configuration. In some embodiments, wherein the first imaging plane configuration includes a first parameter associated with a first beam steering angle, and wherein the second imaging plane configuration includes a second parameter associated with a second beam steering angle less than the first beam steering angle. In some embodiments, wherein the first imaging plane configuration includes a first parameter associated with a first imaging resolution, and wherein the second imaging plane configuration includes a second parameter associated with a second imaging resolution higher than the first imaging resolution. In some embodiments, wherein the determining the second imaging plane configuration includes applying a third predictive network associated with image identification to the third image to generate a second imaging plane configuration, the third predictive network being different from the first predictive network. In some embodiments, wherein the receiving the first image includes receiving, from the ultrasound transducer array, a sequence of images of the patient body, the sequence of images including the first image, and wherein each image of the sequence of images received is based on a different imaging plane configuration, wherein the determining the first imaging plane configuration includes applying the first predictive network to each image of the sequence of images to generate a confidence level associated with a presence of the at least one of the anatomy or the medical device in the image; and selecting the first imaging plane configuration based on the confidence level. In some embodiments, the method further comprises determining a third imaging plane configuration based on the segmentation data, the third imaging plane configuration includes a parameter associated with at least one of beam steering angle, a signal gain, or an imaging depth of field, wherein the displayed image is further based on the third imaging plane configuration.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
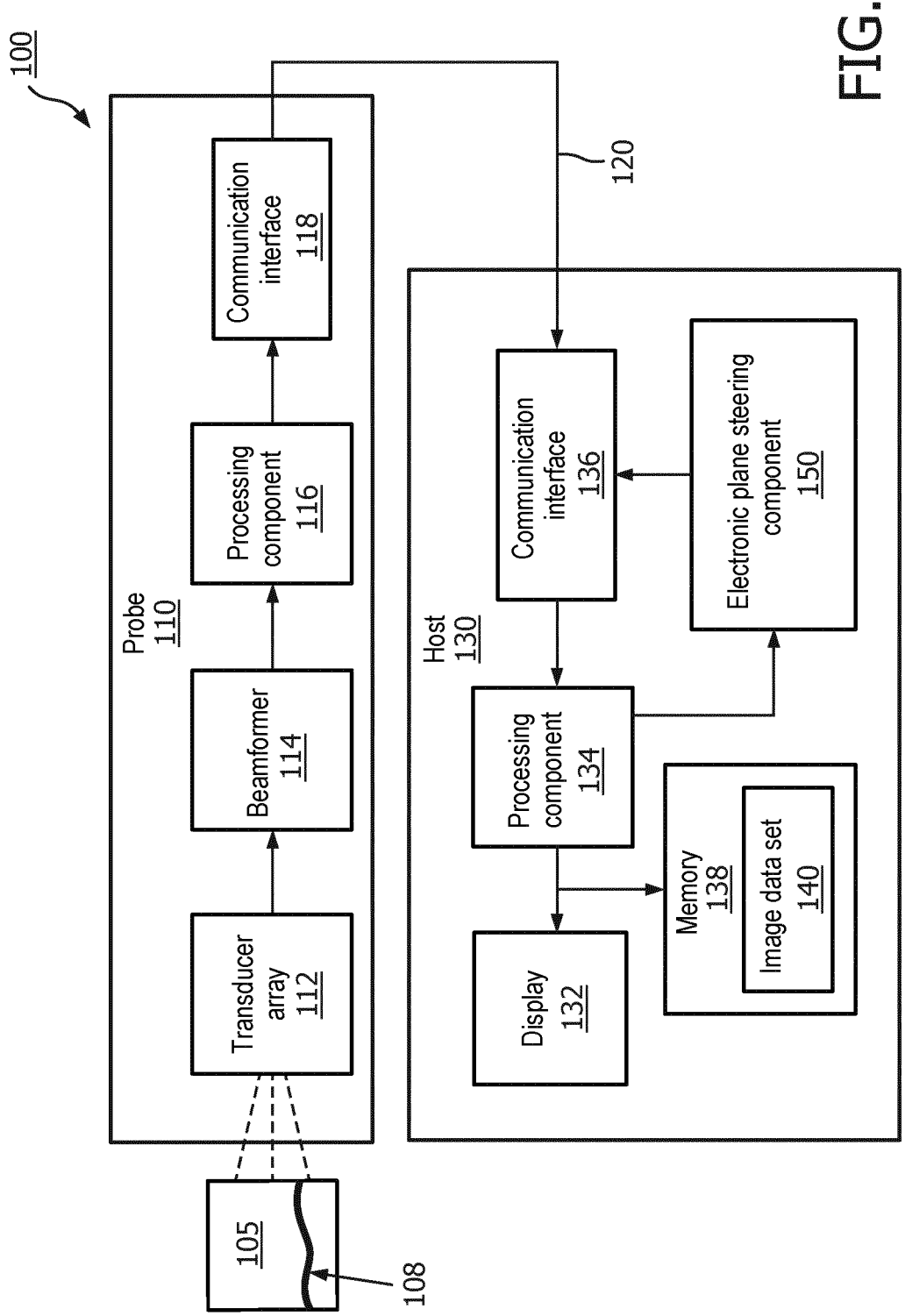
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, and a communication interface 118. The host 130 includes a display 132, a processing component 134, and a communication interface 136.

In an exemplary embodiment, the probe 110 is an external ultrasound imaging device including a housing configured for handheld operation by a user. The transducer array 112 can be configured to obtain ultrasound data while the user grasps the housing of the probe 110 such that the transducer array 112 is positioned adjacent to and/or in contact with a patient's skin. The probe 110 is configured to obtain ultrasound data of anatomy within the patient's body while the probe 110 is positioned outside of the patient's body. In some embodiments, the probe 110 is a transthoracic (TTE) probe. In some other embodiments, the probe 110 can be a trans-esophageal (TEE) ultrasound probe.

The transducer array 112 emits ultrasound signals towards an anatomical object 105 of a patient and receives echo signals reflected from the object 105 back to the transducer array 112. The ultrasound transducer array 112 can include any suitable number of acoustic elements, including one or more acoustic elements and/or plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) that can be uniformly or independently controlled and activated. The transducer array 112 can be configured to obtain one-dimensional, two-dimensional, and/or three-dimensional images of patient anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy, such as blood vessels, nerve fibers, airways, mitral leaflets, cardiac structure, abdominal tissue structure, kidney, and/or liver of a patient that is suitable for ultrasound imaging examination. In some embodiments, the object 105 may include at least a portion of a patient's heart, lungs, and/or skin. In some embodiments, the object 105 may be in constant motion, for example, resulted from breathing, cardiac activities, and/or arterial pulses. The motion may be regular or periodic, for example, with motion of the heart, associated vessels, and/or lungs in the context of a cardiac cycle or a heartbeat cycle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

In some embodiments, the system 100 is used to guide a clinician during a medical procedure (e.g., treatment, diagnostic, therapy, and/or interventions). For example, the clinician may insert a medical device 108 into the anatomical object 105. In some examples, the medical device 108 may include an elongate flexible member with a thin geometry. In some examples, the medical device 108 may be a guide wire, a catheter, a guide catheter, a needle, an intravascular ultrasound (IVUS) device, a diagnostic device, a treatment/therapy device, an interventional device, and/or intracatheter imaging device. In some examples, the medical device 108 may be any imaging device suitable for imaging a patient's anatomy and may be of any suitable imaging modalities, such as optical tomography (OCT), and/or endoscopy. In some examples, the medical device 108 may include a sheath, an imaging device, and/or an implanted device, such as mitral clips. In some examples, the medical device 108 may be a treatment/therapy device including a balloon, a stent, and/or an atherectomy device. In some examples, the medical device 108 may have a diameter that is smaller than the diameter of a blood vessel. In some examples, the medical device 108 may have a diameter or thickness that is about 0.5 millimeter (mm) or less. In some examples, the medical device 108 may be a guide wire with a diameter of about 0.035 inches. In such embodiments, the transducer array 112 can produce ultrasound echoes reflected by the object 105 and the medical device 108.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. The beamforming can reduce the number of signal lines for coupling to the processing component 116. In some embodiments, the transducer array 112 in combination with the beamformer 114 may be referred to as an ultrasound imaging component.

The processing component 116 is coupled to the beamformer 114. The processing component 116 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 116 is configured to process the beamformed image signals. For example, the processing component 116 may perform filtering and/or quadrature demodulation to condition the image signals. The processing component 116 and/or 134 can be configured to control the array 112 to obtain ultrasound data associated with the object 105 and/or the medical device 108.

The communication interface 118 is coupled to the processing component 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processing component 134 is coupled to the communication interface 136. The processing component 134 may be implemented as a combination of software components and hardware components. The processing component 134 may include a central processing unit (CPU), a graphics processing unit (GPU), a digital signal processor (DSP), an application-specific integrated circuit (ASIC), a controller, a FPGA device, another hardware device, a firmware device, or any combination thereof configured to perform the operations described herein. The processing component 134 may also be implemented as a combination of computing devices, e.g., a combination of a DSP and a microprocessor, a plurality of microprocessors, one or more microprocessors in conjunction with a DSP core, or any other such configuration. The processing component 134 can be configured to generate image data from the image signals received from the probe 110. The processing component 134 can apply advanced signal processing and/or image processing techniques to the image signals. In some embodiments, the processing component 134 can form three-dimensional (3D) volume image from the image data. In some embodiments, the processing component 134 can perform real-time processing on the image data to provide a streaming video of ultrasound images of the object 105 and/or the medical device 108.

The display 132 is coupled to the processing component 134. The display 132 may be a monitor or any suitable display. The display 132 is configured to display the ultrasound images, image videos, and/or any imaging information of the object 105 and/or the medical device 108.

The system 100 may be used to provide a clinician with guidance in a clinical procedure. In an example, the system 100 can capture a sequence of ultrasound images of the object 105 and the medical device 108 while the medical device 108 traverses through the object 105 to assist a clinician in performing a clinical procedure. The clinician may be interested in locating a tip of the medical device 108 in the images as the medical device 108 traverses through the object 105. In some example, the medical device 108 may have a sharp tip. Thus, it may be important for the clinician to view and track the movements of the tip to avoid puncturing any anatomy along the pathway of the medical device 108.

The sequence of ultrasound images can be in 2D or 3D. For example, the probe 110 may be a 2D imaging probe including a 1D transducer array 112 that provides 2D images. Alternatively, the probe 110 may be a 3D imaging probe including a 2D transducer array 112 that provides 3D imaging volumes. 3D volumetric imaging has the advantage of providing a full coverage of a 3D volume. Thus, if a certain portion of the object 105 and/or the medical device 108 is within the volumetric field-of-view (FOV), the 3D image may capture the portion of interest. However, 3D volumetric acquisition time and/or processing time can be long. Thus, instead of acquiring 3D volumes at a full image resolution and/or a high frame rate, 3D imaging may typically be performed at a reduced acquisition frame rate and/or a reduced spatial resolution in order to provide real-time 3D imaging. As described above, when the object 105 and/or the medical device 108 have a small size, a thin geometry, and/or a complex structure, visualization of the object 105 and/or the medical device 108 in the 3D volume at the reduced spatiotemporal resolution can be challenging and time-consuming. Further, ultrasound imaging may typically have a high noise level (particularly in the presence of heavy disease) causing even more difficulties or uncertainties in visualization and/or localization of the object 105 and/or the medical device 108.

In an embodiment, the system 100 may utilize a 3D probe 110 to capture 2D image slices in a 3D volume instead of imaging the entire 3D volume. The system 100 may utilize the capability of a 3D probe to steer ultrasound beams to acquire a 2D image slice that is in-plane with the region of interest (e.g., the tip of the medical device 108 and/or a particular portion of object 105). For example, the system 100 may apply a deep learning-based or artificial intelligence (AI)-based closed-loop model to search and locate the region of interest in the 3D volume. The system 100 may iterate between the deep learning-based predictions and corresponding imaging plane steering commands to drive the search. The deep learning-based closed-loop model may perform a series of vision tasks (e.g., device recognition, device tracking, and/or device segmentation and tip localization) that iteratively searches from coarse-to-fine spatial resolution scales and/or imaging resolution scales.

In an embodiment, the processing component 134 may implement a series of prediction networks that perform the series of vision tasks, where the prediction or outputs of one prediction network may be used to initialize a next prediction network in the series of prediction networks. Additionally, the prediction networks can be trained to perform the vision tasks at different spatial resolution scales and/or imaging resolution scales. Further, the predictions or outputs of the prediction networks may be in the form of ultrasound beam steering configurations that can be used to steer ultrasound imaging planes at the probe 110 to provide an optimal visualization of the region of interest.

To provide automatic ultrasound imaging plane steering and the closed-loop search, the system 100 further includes an electronic plane steering component 150 in communication with the probe 110 and the processing component 134. The electronic plane steering component 150 may include hardware and/or software components configured to steer ultrasound beams, configure signal gains, and/or configure depth-of-focus at the probe 110 for imaging. In an example, the processing component 134 can instruct the electronic plane steering component 150 to steer ultrasound beams and/or imaging planes at the probe 110 based on predictions by the prediction networks. While the electronic plane steering component 150 is shown to be part of the host 130, the electronic plane steering component 150 can be outside of the host 130. Mechanisms for providing optimal visualization of a region of interest using a closed-loop deep learning-based ultrasound imaging steering model are described in greater detail herein.

In some embodiments, the system 100 can be used for collecting ultrasound images to form training data set for deep learning network training. For example, the host 130 may include a memory 138, which may be any suitable storage device, such as a cache memory (e.g., a cache memory of the processing component 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory. The memory 138 can be configured to store an image data set 140 to train the series of prediction or deep learning networks for providing optimal object and/or device visualization. Mechanisms for training the series of prediction or deep learning networks are described in greater detail herein.

FIGS. 2-7 collectively illustrate mechanisms for automatic closed-loop ultrasound plane steering for providing optimal target visualization and localization. FIGS. 2-7 are described in the context of providing localization of a tip of a medical device (e.g., the medical device 108). However, similar mechanisms can be used to localize a target anatomical structure (e.g., tortuous blood vessels in distal peripheral anatomy and/or small structures close to the heart that may be affected by cardiac motion).

Figure 2:
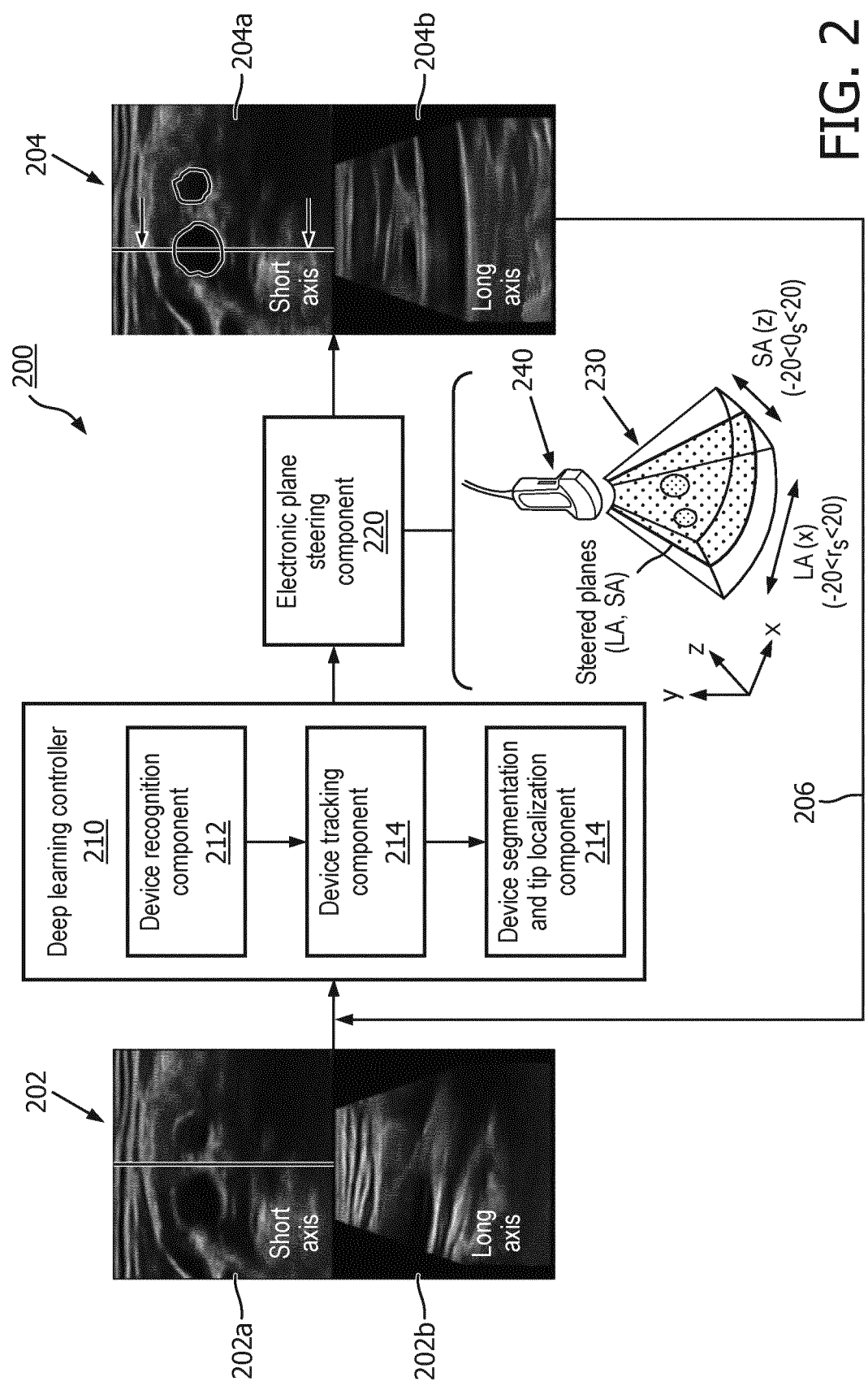
FIG. 2 is a schematic diagram of a deep learning-based automatic closed-loop ultrasound plane steering scheme for providing optimal target visualization, according to aspects of the present disclosure.

FIG. 2 is a schematic diagram of a deep learning-based automatic closed-loop ultrasound plane steering scheme for providing optimal target visualization, according to aspects of the present disclosure. The scheme 200 can be implemented by the system 100. The scheme 200 performs optimal target visualization and localization autonomously without requiring a clinician to perform view finding and/or steering an ultrasound probe. The scheme 200 utilizes a 3D imaging probe 240, a deep learning controller 210, and an electronic plane steering component 220 to provide the optimal target visualization and localization. The probe 240 may be substantially similar to the probe 110. The probe 240 may include a 2D ultrasound transducer array (e.g., the transducer array 112). The electronic plane steering component 220 may be substantially similar to the electronic plane steering component 150. The electronic plane steering component 220 may steer ultrasound beams at the probe 240. The deep learning controller 210 includes a sequence of deep learning/AI-based components including a device recognition component 212, a device tracking component 214, and a device segmentation and tip localization component 216. The device recognition component 212, the device tracking component 214, and the device segmentation and tip localization component 216 can be implemented by a combination of hardware and/or software components. The device recognition component 212, the device tracking component 214, and the device segmentation and tip localization component 216 can be implemented by the processing component 134.

The scheme 200 may be implemented during a clinical procedure. The scheme 200 may acquire ultrasound images 202 of a patient under the clinical procedure using the 3D probe 240. The clinical procedure may require a medical device (e.g., the medical device 108) to be inserted into the patient's anatomy (e.g., the object 105). The medical device may be a needle, a guidewire, catheter, a guide catheter, or any thinly-shaped device. Rather than using the 3D probe 240 to acquire a 3D volume 230 and be limited by the acquisition rate and/or imaging resolution, the 3D probe 240 is configured to acquire the images 202 in a 2D mode. The advantage of using the 3D probe 110 for 2D imaging over a 2D probe is that the 3D probe 240 can be steered to fire ultrasound beams at any angle to capture images at any imaging plane within the 3D volume 230. For example, the 3D probe 240 can capture X-plane images 202 including a short-axis image 202a (e.g., in an y-z plane) and a long-axis image 202b (e.g., in an x-y plane) within the 3D volume 230.

At a high level, the deep learning the device recognition component 212 performs a coarse out-of-plane search over the 3D volume 230 to locate an imaging plane that captures the medical device. The imaging plane may be an out-of-plane imaging plane of the medical device. The out-of-plane refers to the medical device traversing away from a plane of ultrasound waves fired by the probe 240. The device tracking component 214 performs a fine out-of-plane search around the imaging plane determined by the device recognition component 212 to locate an imaging plane that is in-plane with the medical device. The in-plane refers to the medical device traversing along a plane of ultrasound waves fired by the probe 240. The coarse search or the fine search may be in terms of spatial resolution (e.g., ultrasound beam elevation angles) and/or image resolution (e.g., number of pixels in an image). After the device tracking component 214 obtains an image 202 that is in-plane with the medical device, the device segmentation and tip localization component 216 performs in-plane device segmentation on the in-plane image 202 to locate a tip of the medical device or another portion of the medical device that is of interest. In an example, the device recognition component 212, the device tracking component 214, and/or the device segmentation and tip localization component 216 can operate on a combination of long-axis images (e.g., the image 202b) and/or short-axis images (e.g., the image 202a) as described in greater detail herein.

In an embodiment, the device recognition component 212, the device tracking component 214, and the device segmentation and tip localization component 216 may each include a deep learning network. The device recognition component 212 may include a deep learning network trained to identify and/or detect the presence of a medical device in an image. The device tracking component 214 may include a deep learning network trained to track the medical device at a finer imaging plane accuracy (e.g., a distance to an optimal imaging plane) than the device recognition component 212. The device segmentation and tip localization component 216 may include a deep learning network trained to perform image segmentation and device tip localization. The architecture of the deep learning networks in the device recognition component 212, device tracking component 214, and/or the device segmentation and tip localization component 216 are described in greater detail herein.

In some examples, the device recognition component 212 can apply a view classification model for the device identification and/or detection instead of a deep learning model. In some examples, the device tracking component 214 can apply a pose regression model to determine a distance between a current imaging plane an optimal imaging plane instead of a deep learning model. In some examples, the device segmentation and tip localization component 216 can apply other techniques using sensors and tracking for the tip localization instead of a deep learning model. In general, the deep learning controller 210 may utilize a combination of deep learning models and/or other techniques to accomplish the vision tasks of optimal target localization in a manner that searches from a coarse resolution scale to a fine resolution scale. In some embodiments, the deep learning controller 210 may utilize deep learning models for the device recognition component 212 and the device segmentation and tip localization component 216, but may use a pose regression model for the device tracking component 214.

The scheme 200 implements a closed-loop feedback system to provide autonomous optimal target localization and/or visualization. The deep learning controller 210 may iterate between imaging plane predictions and physically controlling the imaging plane (via the electronic plane steering component 220) to perform the search in a closed-loop or feedback loop. For example, the deep learning controller 210 may perform an imaging plane prediction based on an input image (e.g., the short-axis image 202a or the long-axis image 202b) acquired at a first imaging plane. The electronic plane steering component 220 may steer ultrasound beams at the probe 240 based on the imaging plane prediction (e.g., a second imaging plane). After the steering, the probe 240 may acquire an image 204 (e.g., a short-axis image 204a or a long-axis image 204b) at the predicted second imaging plane. The image 204 can be fed back to the deep learning controller 210 for another imaging plane prediction (as shown by the arrow 206). The feedback loop may continue until an in-plane image of the medical device is captured and the tip of the medical device is located. The deep learning controller 210 may activate or exercise one of the device recognition component 212, device tracking component 214, or device segmentation and tip localization component 216 depending on a current stage of the search (e.g., the coarse out-of-plane search, the fine out-of-plane search, or the in-plane search). A more detailed view of operations at the deep learning controller 210 is shown in FIGS. 3-7.

Figure 3:
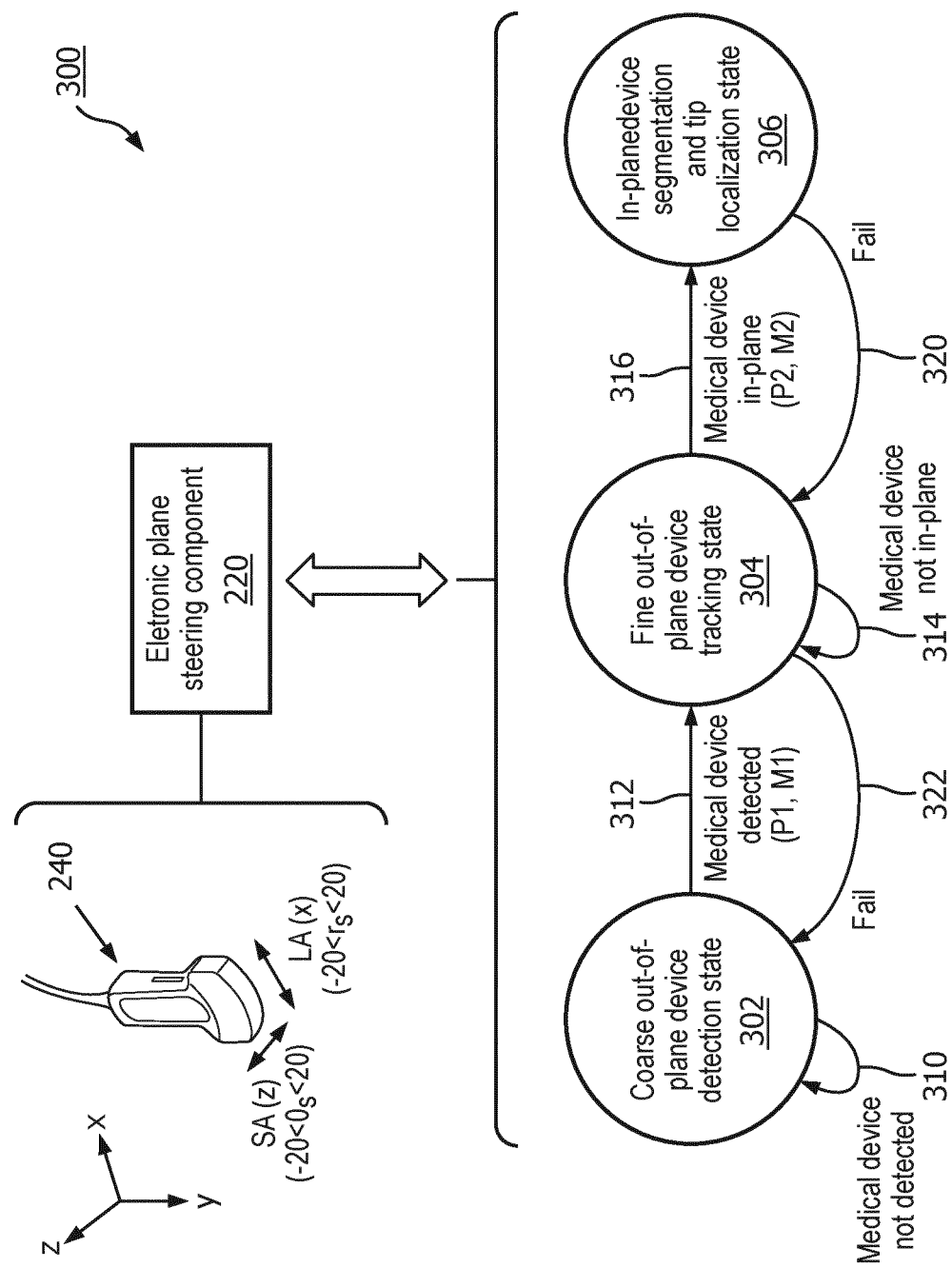
FIG. 3 is a schematic diagram of a deep learning-based automatic closed-loop ultrasound plane steering scheme for providing optimal target visualization, according to aspects of the present disclosure.
Figure 4:
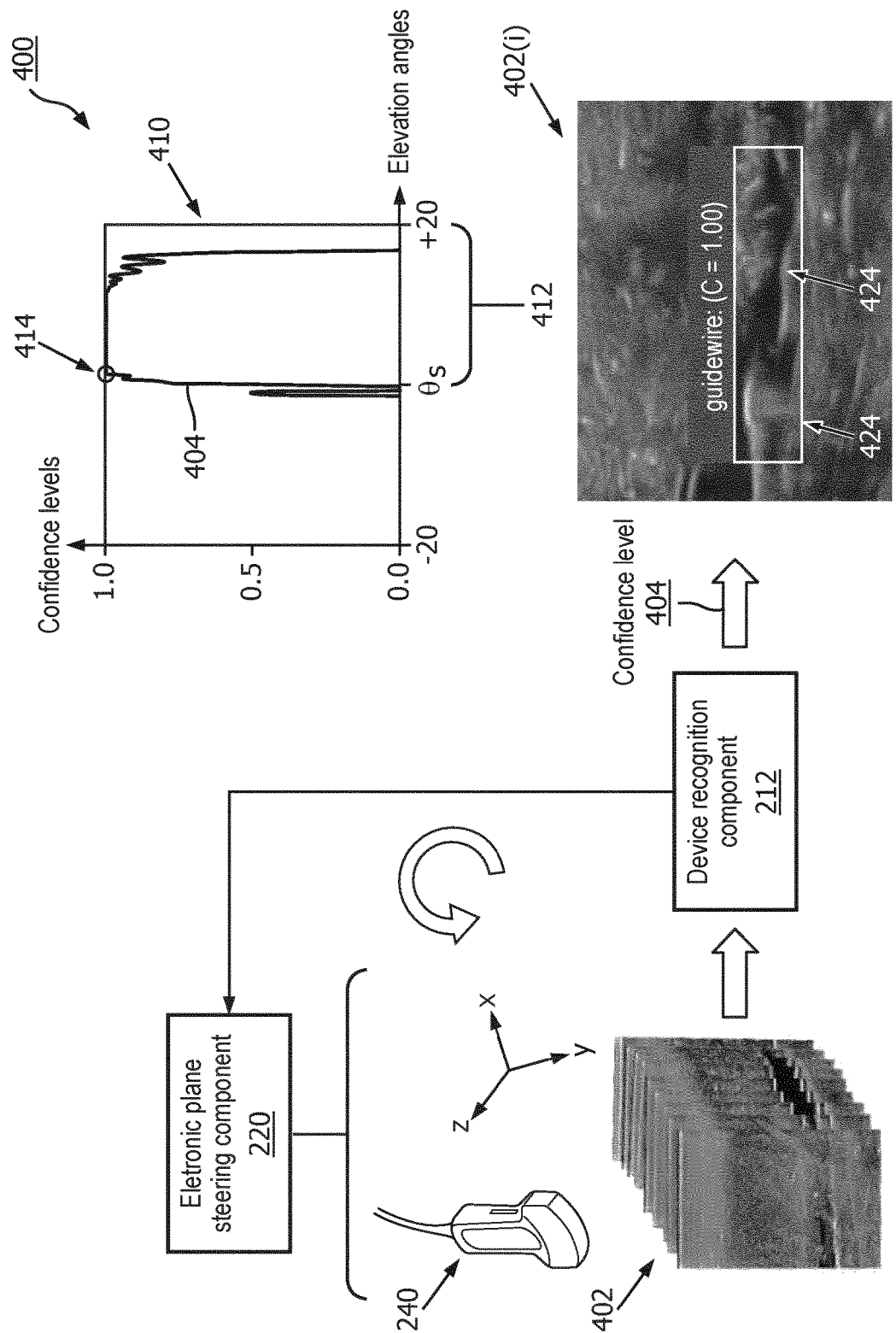
FIG. 4 is a schematic diagram of a deep learning-based device recognition scheme, according to aspects of the present disclosure.
Figure 5:
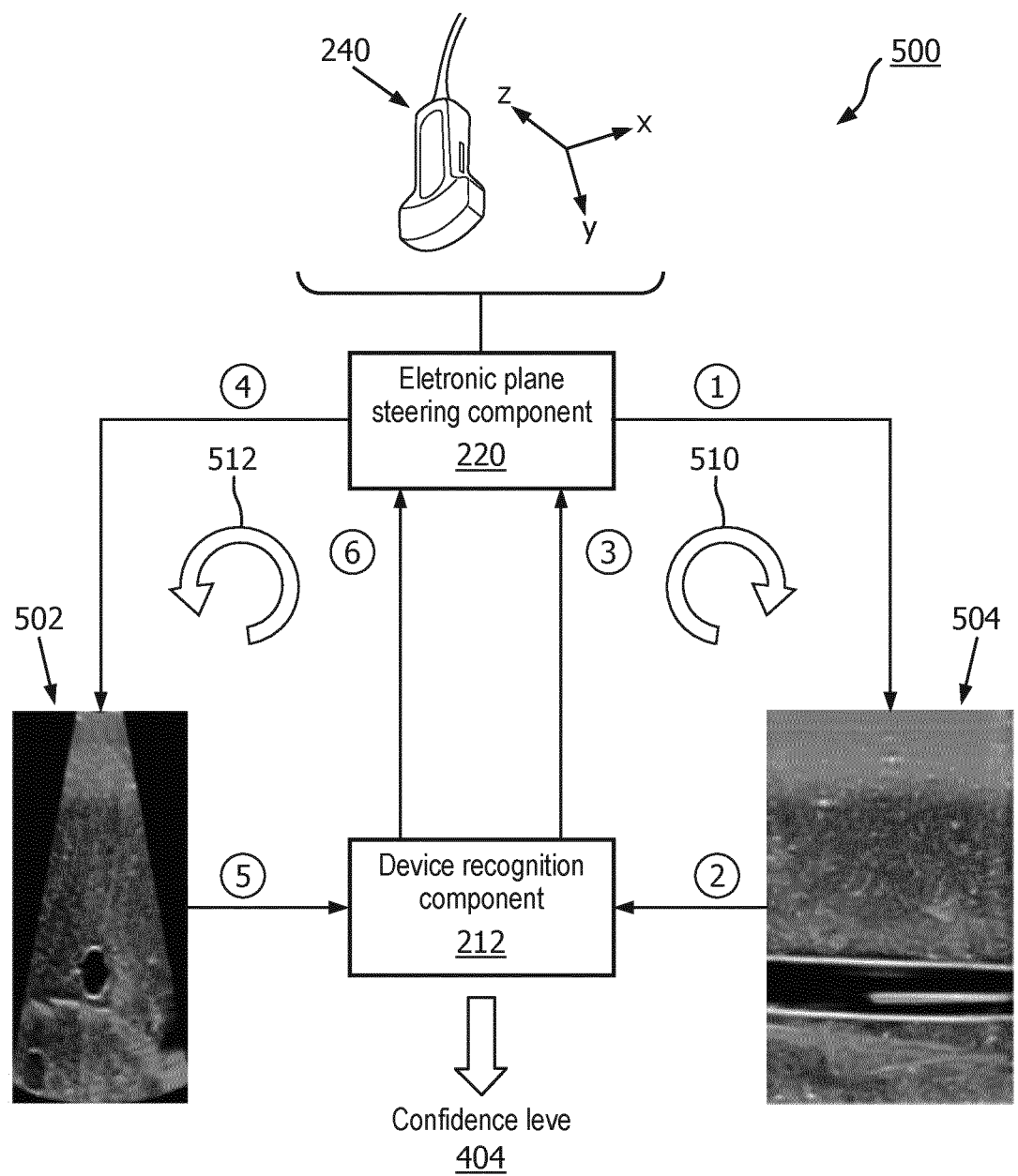
FIG. 5 is a schematic diagram of a deep learning-based device recognition scheme, according to aspects of the present disclosure.
Figure 6:
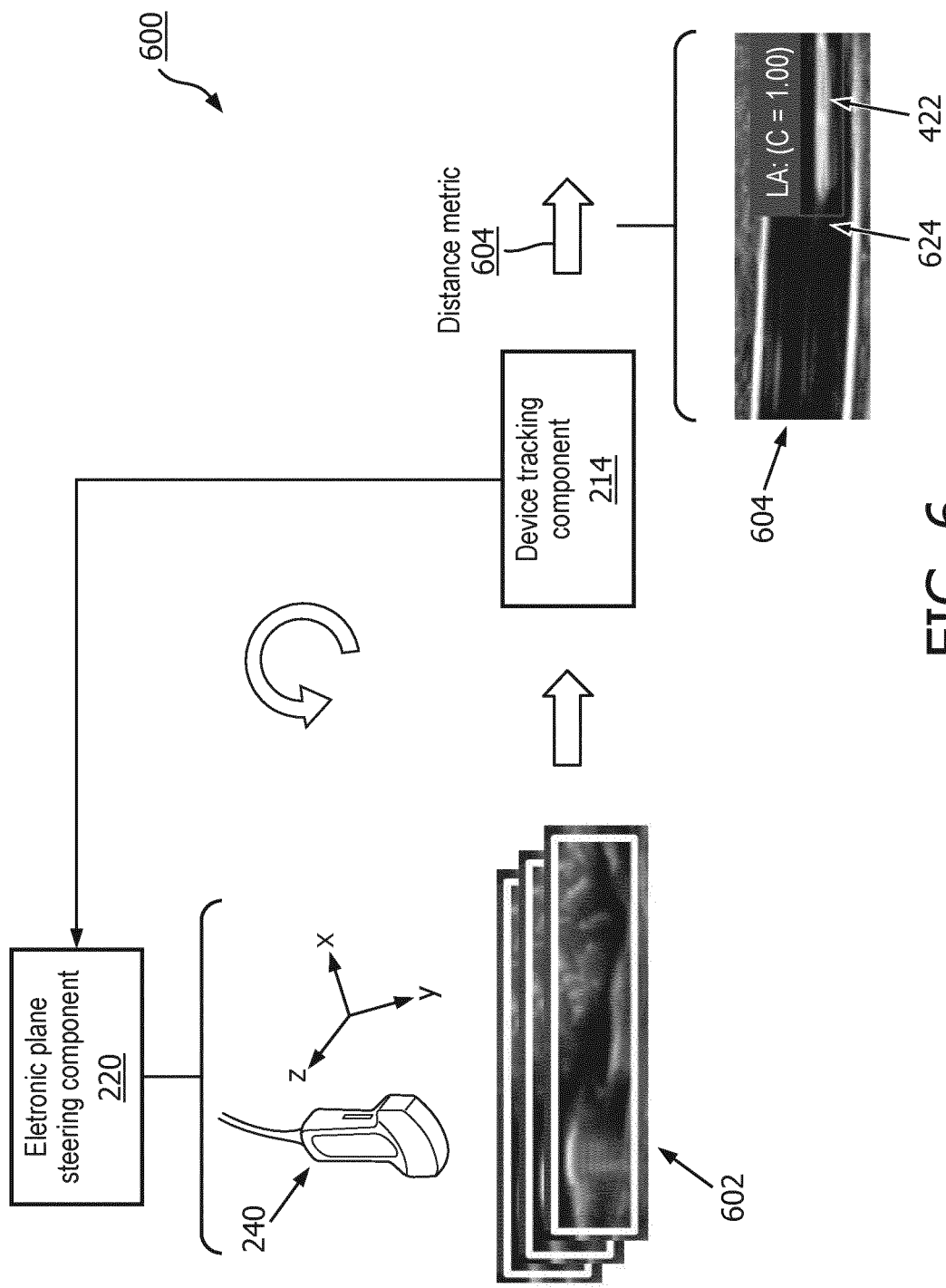
FIG. 6 is a schematic diagram of a deep learning-based device tracking scheme, according to aspects of the present disclosure.
Figure 7:
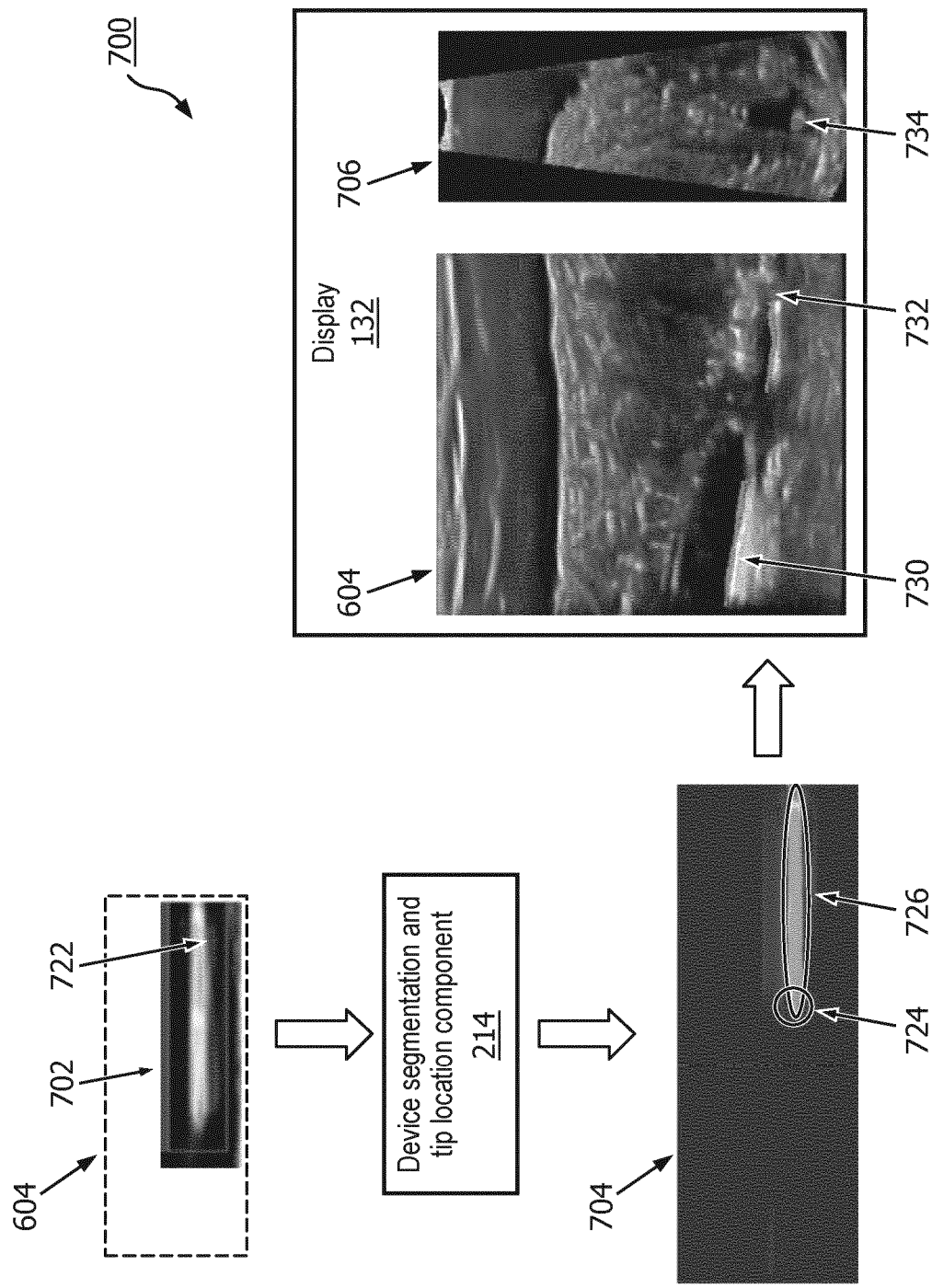
FIG. 7 is a schematic diagram of a deep learning-based device segmentation and tip localization scheme, according to aspects of the present disclosure.

FIG. 3 is a schematic diagram of a deep learning-based automatic closed-loop ultrasound plane steering scheme 300 for providing optimal target visualization, according to aspects of the present disclosure. The scheme 300 is implemented by the deep learning controller 210. The scheme 300 illustrates the transitioning among the different search stages (e.g., the coarse out-of-plane search, the fine out-of-plane search, or the in-plane search). FIG. 4 is a schematic diagram of a deep learning-based device recognition scheme 400, according to aspects of the present disclosure. The scheme 400 is implemented by the device recognition component 212. FIG. 5 is a schematic diagram of a deep learning-based device recognition scheme 500, according to aspects of the present disclosure. The scheme 500 is implemented by the device recognition component 212. FIG. 6 is a schematic diagram of a deep learning-based device tracking scheme 600, according to aspects of the present disclosure. The scheme 600 is implemented by the device tracking component 214. FIG. 7 is a schematic diagram of a deep learning-based device segmentation and tip localization scheme 700, according to aspects of the present disclosure. The scheme 700 is implemented by the device segmentation and tip localization component 216.

Referring to FIG. 3, the deep learning controller 210 may implement a state machine including a coarse out-of-plane device recognition state 302, a fine out-of-plane device tracking state 304, and an in-plane device segmentation and tip localization state 306. The scheme 300 may begin at the coarse out-of-plane device recognition state 302. At the coarse out-of-plane device recognition state 302, the scheme 300 utilizes the device recognition component 212 to perform the coarse resolution search for an approximate location of the medical device within the volumetric FOV. If the device recognition component 212 fails to detect an approximate location of the medical device, the scheme 300 remains in the coarse out-of-plane device recognition state 302 and continue to perform the coarse resolution search as shown by the arrow 310. If the device recognition component 212 detected an image, denoted as M1, at an imaging plane, denoted as P1, including the medical device, the scheme 300 transitions to the fine out-of-plane device tracking state 304 as shown by the arrow 312. The coarse resolution search can be performed based on long-axis images (e.g., the images 202b and 204b) and/or short-axis images (e.g., the images 202a and 204a). If the medical device is well-aligned with the 3D scan plane of the probe 240, then the coarse resolution search can be performed using long-axis images as shown in FIG. 4. If the medical device is foreshortened or inserted in tortuous anatomy, coarse resolution search relying on the long-axis images may not provide an accurate result. Thus, the coarse resolution search may be performed using long-axis images and short-axis images as shown in FIG. 5.

Referring to FIG. 4, the scheme 400 acquires a sequence of long-axis images 402 (e.g., the images 202) by configuring the probe 240 to sweep over a volumetric FOV (e.g., the 3D volume 230) at a large coarse elevational step size (e.g., at increments of about 10 degrees along a direction of the z-axis). For example, the device recognition component 212 may instruct the electronic plane steering component 220 to configure the probe 240 to step through a sequence of elevational angles, denoted as $\theta_s(i)$, and capture an image 402(i) at each imaging plane position $\theta_s(i)$, where i may be a positive integer. In some examples, the coarse out-of-plane search may search the 3D volume at increments of about 10% of the volume, and thus i may vary between 1 to 10.

The device recognition component 212 may be applied to each image 402(i). For each imaging plane position $\theta_s(i)$, the device recognition component 212 may output a confidence level 404 of the image 402(i) including the medical device. The device recognition component 212 may optionally output a bounding box 424 around the portion of the image 402(i) that may include the medical device (e.g., shown as 422 in the image 402(i)). The confidence level 404 is a measure of the prediction correctness or confidence of identifying the medical device. The confidence level 404 may indicate a value between 1 and 0. For example, a confidence level 404 close to 1 may indicate a high likelihood that the bounding box 424 includes the medical device, whereas a confidence level 404 close to 0 may indicate a low likelihood of the bounding box 424 including the medical device. The confidence level 404 may correspond to a confidence level of the bounding box 424 including the medical device. The device recognition component 212 may utilize a deep learning model (e.g., based on a CNN architecture shown in FIG. 8) to predict the confidence levels 404.

A profile of the confidence levels 404 is shown in the plot 410. In the plot 410, the x-axis represents elevational angles $\theta_s(i)$ (e.g., imaging plane positions) and the y-axis represents the confidence levels 404 output by the device recognition component 212. The plot 410 shows elevational angles $\theta_s(i)$ varying between −20 degrees and 20 degrees and confidence levels varying between 0 and 1. As can be observed, several imaging plane positions around a region 412 include noticeably higher confidence levels than other imaging plane positions. The high confidence levels may imply that the imaging plane positions in the region 412 may be centered on the medical device. The optimal imaging plane is determined from the start of the plateau region (e.g., the region 412) of the profile, for example, the imaging plane position 414 (shown as circle symbol).

After determining a confidence level 404 for each image 402(i), the scheme 400 selects the imaging plane position corresponding to an image 402 having the highest confidence level 404 among the images 402 in the sequence. The selected imaging plane position 414 corresponds to an optimal imaging plane (e.g., P1 of FIG. 3) in the coarse resolution search. The image 402 acquired at the selected imaging plane position 414 corresponds to M1 of FIG. 3. The confidence level profile may vary depending on the objects under imaging. Some confidence level profiles may be noisier than others and may have a narrower or less distinct plateau region than the region 412 shown in the plot 410. The task of the device recognition component 212 is to locate a starting position of a plateau region in a confidence level profile.

Referring to FIG. 5, the scheme 500 may be substantially similar to the scheme 400, but the device recognition component 212 is applied to short-axis images 502 in addition to long-axis images 504. Similar to the scheme 400, the scheme 500 may steer the probe 240 along the short-axis (e.g., along a direction of the z-axis) via the electronic plane steering component 220 to acquire long-axis images 504. The steering along the short-axis can be at a relatively large elevational step size. The device recognition component 212 may be applied to each long-axis image 504 to determine a confidence level 404 of the image 504 including a medical device 522 (e.g., the medical devices 108 and 422). The device recognition component 212 may select an imaging position along the short-axis with the highest confidence level 404 using similar mechanisms as in the scheme 400. The search along the short-axis is shown by the arrow 510 with steps 1-3 (shown by the circled numerals).

Subsequently, the scheme 500 may steer the probe 240 to sweep along the long-axis (e.g., along a direction of the x-axis) via the electronic plane steering component 220 to acquire a series of short-axis images 502. Similarly, the steering along the long-axis can be at a relatively large lateral step size. The device recognition component 212 may be applied to each short-axis image 502 to determine a confidence level 404 of the image 502 including the medical device. The search along the long-axis is shown by the arrow 512 with steps 4-5 (shown by the circled numerals). In the scheme 500, the device recognition component 212 may utilize a deep learning model trained to recognize object of two classes: a device in the short-axis (with short cross-sectional artifact) and in the long-axis (with a high intensity linear artifact) to predict the confidence levels 404.

In general, the scheme 500 may iterate along the short-axis and the long-axis in any order until each of the acquired short-axis image 502 and the long-axis image 504 (e.g., M1 of FIG. 3) at a particular X-plane imaging position (e.g., P1 of FIG. 3) provide a sufficiently high confidence levels 404.

Returning to FIG. 3, after locating an optimal long-axis imaging plane P1 from the coarse out-of-plane device recognition state 302, the scheme 300 may steer the probe 240 to the optimal long axis imaging plane P1 (via the electronic plane steering component 220). At the fine out-of-plane device tracking state 304, the scheme 300 utilizes the device tracking component 214 to iterate between imaging plane predictions and physically controlling the imaging plane of the probe 240 (via the electronic plane steering component 220) to perform a fine search around the imaging plane P1 determined at the coarse out-of-plane device recognition state 302. The task of the device tracking component 214 is to locate an imaging plane that is in-plane with the medical device (e.g., as shown in FIG. 6). If the device tracking component 214 cannot find an imaging plane in-plane with the medical device, the scheme 300 remains in the ds fine out-of-plane device tracking state 304 and continue to perform the fine search as shown by the arrow 314. If the device tracking component 214 found an imaging plane P2 with an acquired image M2 that is in-plane with the medical device, the scheme 300 transitions to the device segmentation and tip localization state 306 as shown by the arrow 316.

Referring to FIG. 6, the scheme 600 begins at the optimal long-axis imaging plane P1 determined by the scheme 400 and/or 500 in the coarse out-of-plane device recognition state 302. In an example, the device tracking component 214 may operate on a cropped image 602 corresponding the portion of the image M1 within the bounding box (e.g., the bounding box 424) where the medical device is detected. The device tracking component 214 may perform the fine search or adjustment on a frame-by-frame basis. The device tracking component 214 determines a distance offset between the current imaging plane and the ground truth in-plane imaging plane for capturing the medical device and instructs the electronic plane steering component 220 to steer the probe 240 according to the determined distance offset. After the steering, the probe 240 may acquire another image 602 and repeat the process in a closed-loop form until an-plane imaging plane is reached. In an example, the adjustment may be in units of millimeter (mm) (e.g., <2 mm).

Figure 8:
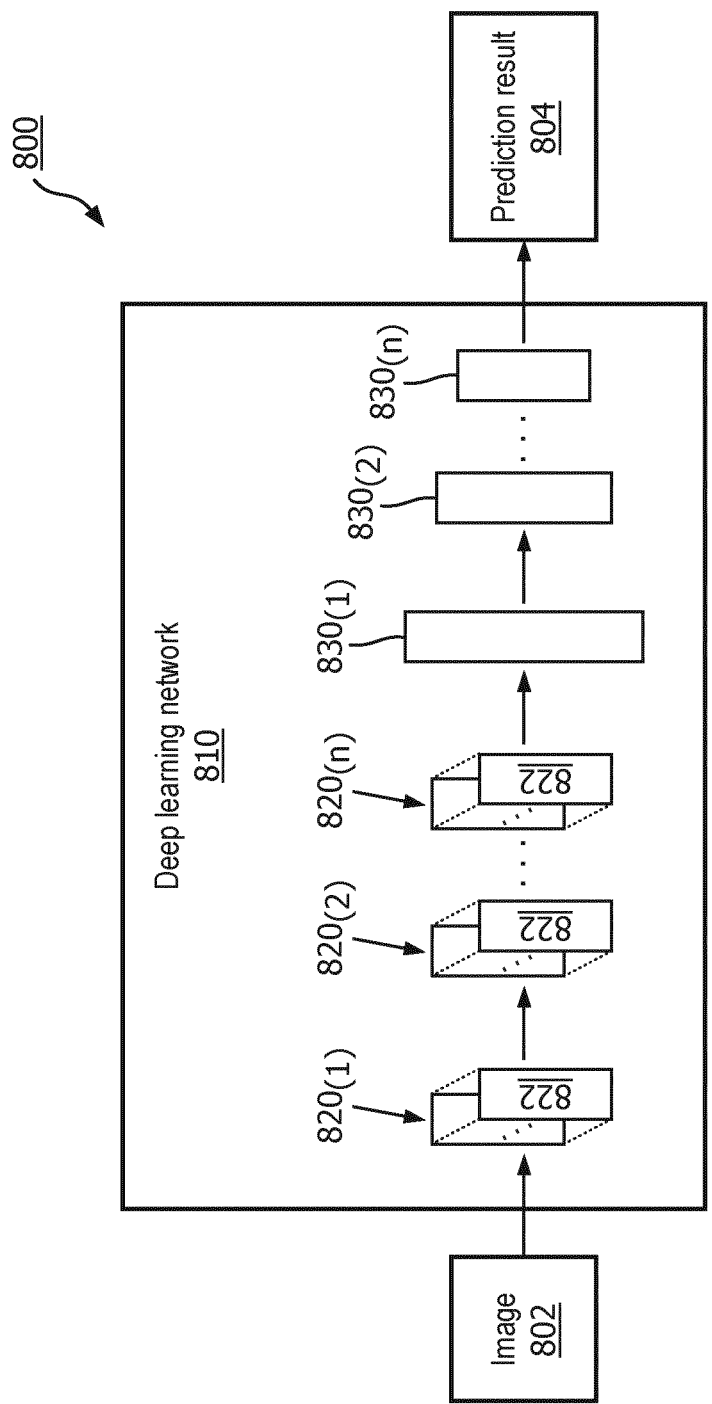
FIG. 8 is a schematic diagram of a deep learning network configuration, according to aspects of the present disclosure.

In an embodiment, the device tracking component 214 may compute the distance offset in each image 602 by employing a pose regression network (e.g., based on a CNN architecture shown in FIG. 8). The pose regression network may perform regression of offset in the long axis (e.g., the different between the ground truth or in-plane imaging plane and the current imaging plane). To use the network, the bounding box (e.g., the bounding box 424) from the image M1 is automatically extended to the entire lateral width of the image to generate a region of interest (ROI) where the medical device is positioned. The image M1 is cropped to the ROI and input into the regression network. Cropping in this manner allows the ROI determined in the coarse out-of-plane device recognition state 302 to be used to constrain the predictions in the fine out-of-plane device tracking state 304. Specifically, it allows irrelevant information that is not part of the medical device to be disregarded. Additionally, the cropping can eliminate artefacts or confounding structure that lie outside the ROI. The medical device pose relative to the current imaging frame is updated from frame to frame based on the network predictions, allowing real-time adjustment of imaging plane to account for small out-of-plane motions of the medical device or the probe 240, for example, as the medical device is actively being navigated or moved.

While the scheme 600 illustrates the fine search performed on long-axis images, the scheme 600 can additionally utilize short-axis images for the fine search. For example, the scheme 600 may acquire a short-axis image (e.g., the images 204a an d502) at the optimal long-axis imaging plane M1 (e.g., the imaging plane position 414 of FIG. 4). The device tracking component 214 may determine the distance offset to the ground truth or optimal in-plane imaging plane using the short-axis image.

At the end of the fine search, the scheme 600 reaches an optimal in-plane imaging plane (e.g., P2 of FIG. 3) of the medical device and obtains an optimal in-plane image 604 (e.g., M2 of FIG. 3) of the medical device at the in-plane imaging plane. Additionally, the device tracking component 214 may output a bounding box 624 around the medical device (shown as 622) in the optimal in-plane image 604.

Returning to FIG. 3, after obtaining an in-plane imaging plane P2 of the medical device from the fine out-of-plane device tracking state 304, the scheme 300 utilizes the device segmentation and tip localization component 216 to segment the medical device in the image M2 and localizes the medical device tip from the image M2 (e.g., as shown in FIG. 7). The segmentation and localization can provide useful information for guiding interventions.

Referring to FIG. 7, the scheme 700 performs device segmentation and tip localization on the optimal in-plane image M2 604. The device segmentation and tip localization component 216 may operate on a cropped image 702 corresponding to the portion of the image M2 604 within the bounding box 624 where the medical device (shown as 722) is identified. For example, the bounding box 624 is extended to the entire lateral width of the image to generate the device ROI for cropping. In some other examples, the cropping can be a soft cropping, where higher weights may be applied to the portion of the image within the bounding box 624 and lower weights may be applied to the portion of the image outside of the bounding box 624. The device segmentation and tip localization component 216 may use a deep learning network (e.g., based on a convolutional encoded-decoder architecture shown in FIG. 9) for device segmentation and tip localization. In an embodiment, the network may perform pixel-wise classification and output a prediction or score (e.g., ranging between 0 and 1) for each pixel (e.g., ranging between 0 and 1) indicating whether the pixel includes the medical device. For example, a pixel with prediction score close to 1 may indicate that the pixel is likely to include the medical device. On the hand, a pixel with prediction score close to 0 may indicate that the pixel is unlikely to include the medical device. As shown, the device tracking component 214 produces an output image 704 where a region 726 or portion of the output image 704 with prediction scores close to 1. Thus, the medical device tip 724 can be automatically localized at the distal end of the region 726. In another embodiment, the network may output a positional x-y coordinate in the image 702 where the device tip 724 localized.

After localizing the medical device tip 724, the scheme 700 may further acquire a short-axis image 706 at the optimal in-plane imaging plane P2. The scheme 700 may display the optimal long-axis image 604 and an optimal short-axis image 706 at the display 132. The scheme 700 may provide visual indications of the medical device 722 and/or the medical device tip 724 in the long-axis image 604 and the short-axis image 706 based on the output 704. For example, the scheme 700 may utilize a green color line (shown as 730) and a red color dot (shown as 732) overlaid on top of the long-axis image 604 to indicate the detected medical device 722 and the medical device tip 724, respectively. The scheme 700 may utilize a red color dot (shown as 734) overlaid on top of the short-axis image 706 to indicate the medical device tip 724. In general, the scheme 700 may use indicators or markings of any shape and any color or any suitable color map to indicate or highlight the medical device and the medical device tip within the optimal long-axis image 604 and the optimal short-axis image 706.

Returning to FIG. 3, if a failure is detected during any state 302, 304, or 306, the scheme 300 may return to a previous state. For example, if the visibility of the medical device is lost during the in-plane device segmentation and tip localization state 306, the scheme 300 may return to the previous fine out-of-plane device tracking state 304 as shown by the arrow 320. The device tracking component 214 may apply the pose regression network to fine-tune the steering angle of the probe 240 to reinstate optimal device visualization. Similarly, if the visibility of the medical device is lost during the fine out-of-plane device tracking state 304, the scheme 300 may return to the previous coarse out-of-plane device recognition state 302 as shown by the arrow 322.

While the schemes 200-700 are described the coarse-to-fine search in terms of spatial resolutions (e.g., elevation and/or lateral step size), the schemes 200-700 may apply the coarse-to-fine search in terms of imaging resolution. For example, the coarse out-of-plane device recognition state 302 may apply the device recognition component 212 to images of a low imaging resolution (e.g., with a down-sampling factor of 8), the fine out-of-plane device tracking state 304 may apply the device tracking component 214 to images at a moderate imaging resolution (e.g., with a down-sampling factor of 4), and the in-plane device segmentation and tip localization state 306 may apply the device segmentation and tip localization component 216 to images at a high imaging resolution (e.g., full resolution). The acquisition time and processing of a lower resolution image can be faster the acquisition time and/or processing time of a higher resolution image, and thus may speed up the search in the coarse out-of-plane device recognition state 302 and/or the fine out-of-plane device tracking state 304.

FIG. 8 is a schematic diagram of a deep learning network configuration 800, according to aspects of the present disclosure. In an example, the configuration 800 can be implemented by the device recognition component 212 for device recognition. In another example, the configuration 800 can be implemented by the device tracking component 214 for device tracking. The configuration 800 includes a deep learning network 810. The deep learning network 810 may be referred to as a convolutional neural network (CNN). The deep learning network 810 may include a set of N convolutional layers 820 followed by a set of K fully connected layers 830, where N and K may be any positive integers. The convolutional layers 820 are shown as $820_{(1)}$ to $820_{(N)}$. The fully connected layers 830 are shown as $830_{(1)}$ to $830_{(K)}$. Each convolutional layer 820 may include a set of filters 822 configured to extract imaging features (e.g., the medical device 108, 422, and, 522) from an input image 802 (e.g., the images 202, 402, 502, 602, and 702). The values N and K and the size of the filters 822 may vary depending on the embodiments. In an example, the convolutional layers $820_{(1)}$ to $720_{(N)}$ and the fully connected layers 730 $730_{(1)}$ to $730_{(K-1)}$ may utilize a leaky rectified non-linear (ReLU) activation function and/or batch normalization. The fully connected layers 830 may be non-linear and may gradually shrink the high-dimensional output to a dimension of the prediction result 804.

The input image 802 may be passed through each layer 820 and 830 in succession for feature extraction, analysis, and/or classification. Each layer 820 or 830 may include weightings (e.g., filter coefficients for the filters 822 in the convolutional layers 820 and non-linear weightings for the fully-connected layers 830) that are applied to the input image 802 or an output of a previous layer 820 or 830.

In an embodiment, the device recognition component 212 may include the deep learning network 810. The deep learning network 810 may be applied to an ultrasound image (e.g., the images 202, 402, and/or 502) to determine whether the image captures a medical device (e.g., the medical device 108). In such an embodiment, the prediction result 804 may include a value between 1 and 0 representing the likelihood or confidence level of the image capturing the medical device.

To train the deep learning network 810 for device recognition, a training data set (e.g., the image data set 140) can be created, for example, including a sequence of ultrasound images (e.g., 2D, X-plane, and/or multi-plane images similar to the images 202, 402, and/or 502) captured by a 3D probe (e.g., the probe 240). The ultrasound images may be images of a phantom, a live patient, and/or a cadaver and may include various types of thinly-shaped medical devices. The training data may associate each image with a ground truth indicating whether the image captures the medical device. The deep learning network 810 can be applied to each image in the data set, for example, using forward propagation, to obtain an output or a score for the input image. The coefficients of the filters 822 in the convolutional layers 820 and weightings in the fully connected layers 830 can be adjusted, for example, by using backward propagation to minimize a prediction error (e.g., a difference between the ground truth and the prediction result 804).

In an embodiment, the device tracking component 214 may include the deep learning network 810. The deep learning network 810 may be applied to an ultrasound image (e.g., the images 602) to determine a distance offset between a current imaging plane and an in-plane imaging plane of a medical device (e.g., the medical device 108). In such an embodiment, the prediction result 804 may include a distance metric (e.g., in units of mm).

To train the deep learning network 810 for device tracking, a training data set (e.g., the image data set 140) can be created, for example, including a sequence of ultrasound images (e.g., 2D, X-plane, and/or multi-plane images similar to the images 202, 402, and/or 502) captured by a 3D probe (e.g., the probe 240). The ultrasound images may be images of a phantom, a live patient, and/or a cadaver and may include various types of thinly-shaped medical devices. The training data may associate each image with a ground truth indicating a distance or offset to an in-plane imaging plane of the medical device. The deep learning network 810 can be applied to each image in the data set, for example, using forward propagation, to obtain an output or a score for the input image. The coefficients of the filters 822 in the convolutional layers 820 and weightings in the fully connected layers 830 can be adjusted, for example, by using backward propagation to minimize a prediction error (e.g., a difference between the ground truth distance offset and the prediction result 804).

Figure 9:
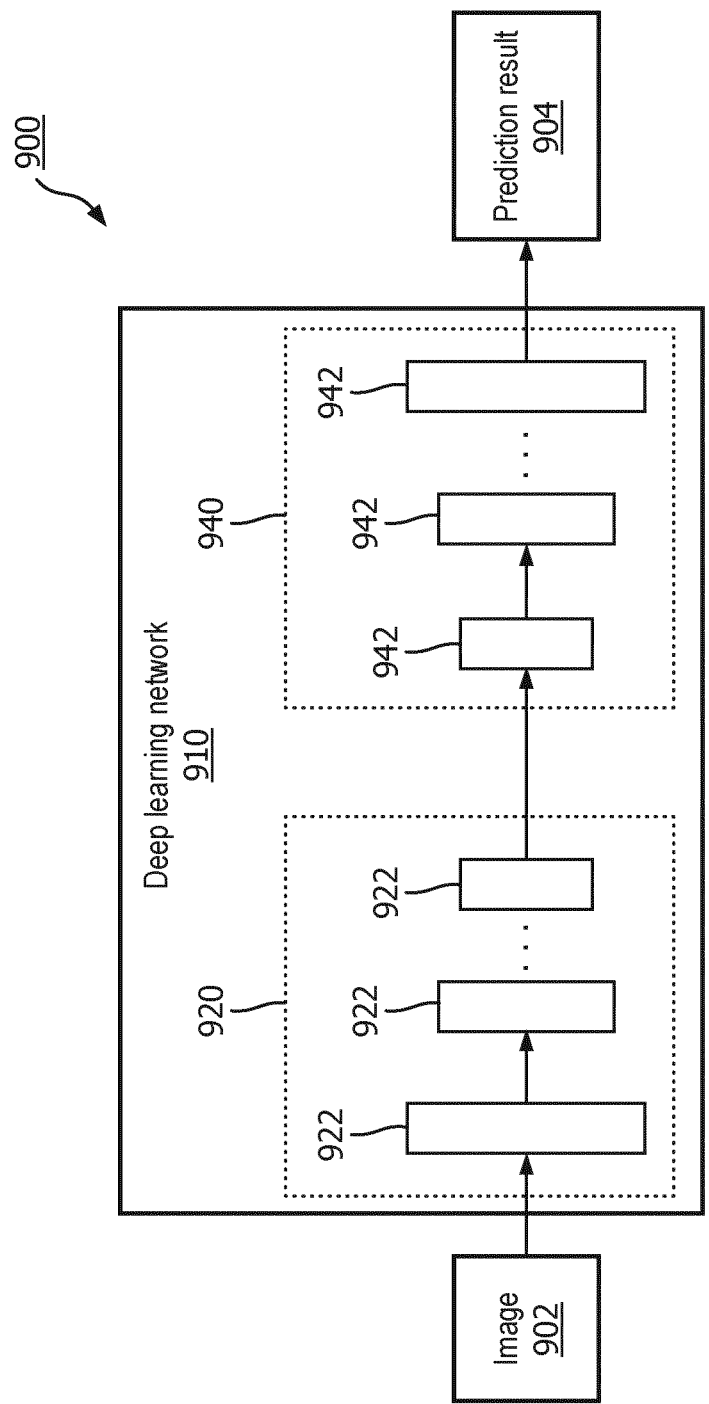
FIG. 9 is a schematic diagram of a deep learning network configuration, according to aspects of the present disclosure.

FIG. 9 is a schematic diagram of a deep learning network configuration 900, according to aspects of the present disclosure. In an example, the configuration 900 can be implemented by the device segmentation and tip localization component 216. The configuration 900 includes a deep learning network 910. The deep learning network 910 includes a convolutional encoder 920 and a convolutional decoder 940. The convolutional encoder 920 includes a plurality of convolutional encoding layers 922. The convolutional decoder 940 includes a plurality of convolutional decoding layers 942. In some examples, the number of convolutional encoding layers 922 and the number of convolutional decoding layers 942 may be the same. In some examples, the number of convolutional encoding layers 922 and the number of convolutional decoding layers 942 may be different or the same depending on the embodiments.

The convolutional encoding layers 922 and the convolutional decoding layers 942 may be substantially similar to the convolutional layers 820. For example, each of the convolutional encoding layers 922 and each of the convolutional decoding layers 942 may include a convolutional filter or kernel. The convolutional kernel can be a 2D kernel. The filter coefficients for the convolutional kernels are trained to perform segmentation and device tip localization in an input image 902 (e.g., the in-plane image 604). Additionally, each convolutional encoding layer 922 may be followed by a down-sampling layer. Each convolutional decoding layer 942 can be preceded by an up-sampling layer. The down-sampling and up-sampling can be at any suitable factor. In some examples, the down-sampling factor at each down-sampling layer and the up-sampling factor at each up-sampling layer can be about 2. The convolutional encoding layers 922 and the convolutional decoding layers 942 can be trained to extract features from the 902 at different spatial resolutions. In an embodiment, the deep learning network 910 outputs a prediction result 904 including pixel-wise classification information. For example, the prediction result 904 may include a score (e.g., ranging between 0 and 1) for each pixel (e.g., ranging between 0 and 1) indicating whether the pixel includes the medical device.

The input image 902 may be passed through each convolutional encoding layer 922 and convolutional decoding layers 942 in succession for feature extraction, analysis, and/or classification for device segmentation and tip localization. Each layer 922 and 942 may include weightings (e.g., filter coefficients) that are applied to the input image 902 or an output of a previous layer 922 or 942.

In an embodiment, the device tracking component 214 may include the deep learning network 910. The deep learning network 910 may be applied to an ultrasound image (e.g., the in-plane image 604) to segment a medical device (e.g., the medical device 108) in the image and localize a tip of the medical device. To train the deep learning network 910 for device segmentation and tip localization, a training data set (e.g., the image data set 140) can be created, for example, including a sequence of ultrasound images (e.g., 2D, X-plane, and/or multi-plane images similar to the images 202, 402, and/or 502) captured by a 3D probe (e.g., the probe 240). The ultrasound images may be images of a phantom, a live patient, and/or a cadaver and may include various types of thinly-shaped medical devices. The training data may associate each image with a ground truth for each pixel in the image indicating whether the pixel captures the medical device and the location of the medical device tip. The deep learning network 910 can be applied to each image in the data set, for example, using forward propagation, to obtain an output or a score for the input image. The coefficients of the 2D filter kernels in the convolutional encoding layers 922 and the convolutional decoding layers 942 can be adjusted, for example, by using backward propagation to minimize a prediction error (e.g., a difference between the ground truth and the prediction result 804).

In an embodiment, while the schemes 200-700 illustrate the deep learning controller 210 implementing three separate deep learning networks for device recognition, device tracking, and device segmentation and tip localization, the deep learning controller 210 may implement a single deep learning network trained to perform the tasks of device recognition, device tracking, and device segmentation and tip localization. The single deep learning network may iterate between predicting imaging planes and physically controlling the probe 240 using substantially similar mechanisms as described above. The use of a single deep learning network may allow for the network to be trained and optimized jointly for the tasks of device recognition, device tracking, and device segmentation and tip localization.

In an embodiment, the schemes 200-700 may begin after the probe 240 is positioned at an approximate location where the object of interest may be located. The initial location approximation may be performed using any suitable mechanism. By positioning the probe 240 at an approximate location of the object of interest may greatly reduce the number of iterations required to steer the probe 240, and thus can reduce the amount of time in reaching the optimal imaging plane.

While the schemes 200-700 illustrate target localization using long-axis images and/or short-axis images as inputs to the deep learning controller 210, similar mechanisms can be applied to inputs with multiplanar images and/or small 3D-subvolumes. For example, the deep learning controller 210 may be trained to perform device recognition, device tracking, and device segmentation and tip localization on multiplanar images and/or 3D-subvolumes. Additionally, the schemes 200-700 can further utilize temporal information to further improve the prediction performance. For example, the device recognition component 212, the device tracking component 214, and the device segmentation and tip localization component 216 can predict an imaging plane configuration based on a sequence of images acquired over a time period instead of a long-axis image and/or a short-axis image captured at single point in time.

Figure 10:
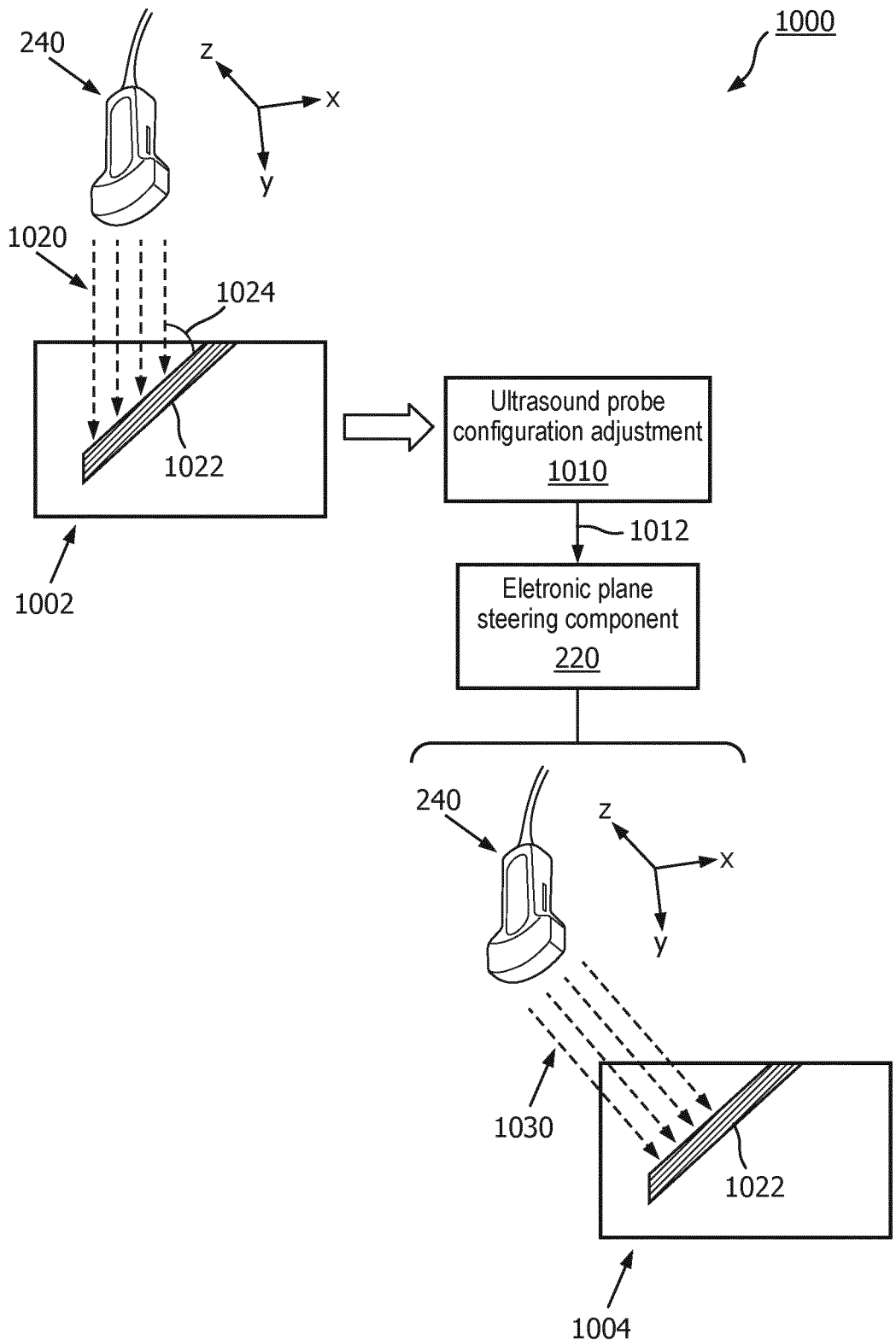
FIG. 10 is a schematic diagram of an ultrasound imaging configuration scheme, according to aspects of the present disclosure.

FIG. 10 is a schematic diagram of an ultrasound imaging configuration scheme 1000, according to aspects of the present disclosure. The scheme 1000 can be implemented by the system 100, for example, implementing the device segmentation and tip localization as shown in the scheme 700 discussed above. For example, while the device tracking component 214 may steer the probe 240 to capture an image (e.g., the image 604) in-plane with the medical device for device segmentation and tip localization, the ultrasound beams fired by the probe 240 may not be perpendicular to the medical device. As an example, the device segmentation and tip localization component 216 may operate on an image 1002 where ultrasound beams 1020 are emitted at any angle 1024 to a medical device 1022 (e.g., the medical device 108). While the device segmentation and tip localization component 216 may segment the medical device 1022 and localize a tip of the device, the image 1002 may not provide the best visibility of the medical device 1022. The scheme 1000 may include an ultrasound probe configuration adjustment component 1010 configure to compute ultrasound beam angle adjustment 1012 so that the probe 240 may fire ultrasound beams about perpendicular to the medical device 1022. The ultrasound probe configuration adjustment component 1010 may instruct the electronic plane steering component 220 to steer the probe 240 according to the adjustment 1012. After the steering, the probe 240 may acquire an image 1004 where the ultrasound beams 1030 fired by the probe 240 are perpendicular to the medical device 1022.

While the scheme 1000 is described in the context of beam angle adjustment after device segmentation and tip localization, similar mechanisms may be applied to adjust the signal gain of the ultrasound beams, a depth-of-focus, dynamic range, imaging depth, image cropping, region-of-interests for Doppler imaging or other modalities, and/or any other ultrasound transmission parameters to further improve the visibility of the medical device. In some aspects, the segmentation can also be used to initialize other quantifications, for example, initialization of a separate segmentation of anatomical structures in which the device is located.

In some embodiments, the system 100 may additionally provide voice command functionalities for driving the closed-loop ultrasound imaging plane steering mechanisms described above in the schemes 200-700 and 1000. For example, the host 130 may include a microphone configured to receive a user voice command and the processing component 134 may implement a voice recognition algorithm to detect a user input command and in turn drive the closed-loop search. A user may voice a command to start the closed-loop search and the system 100 may step through the coarse out-of-plane device recognition state 302, the fine out-of-plane device tracking state 304, the in-plane device segmentation and tip localization state 306 as described above until an optimal imaging plane of the medical device is reached and may provide optimal visualization of the medical device and localization of the medical device tip. Additionally or alternatively, the system 100 may include other interfaces, such as cameras, sensors, touch screen interface, and/or buttons on the probe 110, to allow a user to initiate a certain stage of the closed-loop search via gestures, eye-tracking based commands, a tap on the touch screen, and/or pressing the button on the probe 110.

Figure 11:
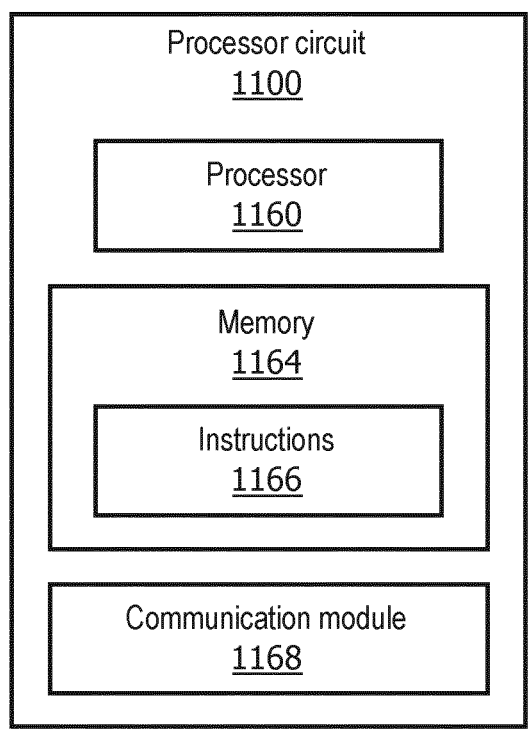
FIG. 11 is a schematic diagram of a processor circuit, according to embodiments of the present disclosure.

FIG. 11 is a schematic diagram of a processor circuit 1100, according to embodiments of the present disclosure. The processor circuit 1100 may be implemented in the probe 110 and/or the host 130 of FIG. 1. In an example, the processor circuit 1100 may be in communication with the transducer array 112 in the probe 110. As shown, the processor circuit 1100 may include a processor 1160, a memory 1164, and a communication module 1168. These elements may be in direct or indirect communication with each other, for example via one or more buses.

The processor 1160 may include a CPU, a DSP, an application-specific integrated circuit (ASIC), a controller, an FPGA, another hardware device, a firmware device, or any combination thereof configured to perform the operations described herein, for example, aspects of FIGS. 2-10 and 12. The processor 1160 may also be implemented as a combination of computing devices, e.g., a combination of a DSP and a microprocessor, a plurality of microprocessors, one or more microprocessors in conjunction with a DSP core, or any other such configuration.

The memory 1164 may include a cache memory (e.g., a cache memory of the processor 1160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 1164 includes a non-transitory computer-readable medium. The memory 1164 may store instructions 1166. The instructions 1166 may include instructions that, when executed by the processor 1160, cause the processor 1160 to perform the operations described herein, for example, aspects of FIGS. 2-10 and 12 and with reference to the probe 110 and/or the host 130 (FIG. 1). Instructions 1166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 1168 can include any electronic circuitry and/or logic circuitry to facilitate direct or indirect communication of data between the processor circuit 1100, the probe 110, and/or the display 132. In that regard, the communication module 1168 can be an input/output (I/O) device. In some instances, the communication module 1168 facilitates direct or indirect communication between various elements of the processor circuit 1100 and/or the probe 110 (FIG. 1) and/or the host 130 (FIG. 1)

Figure 12:
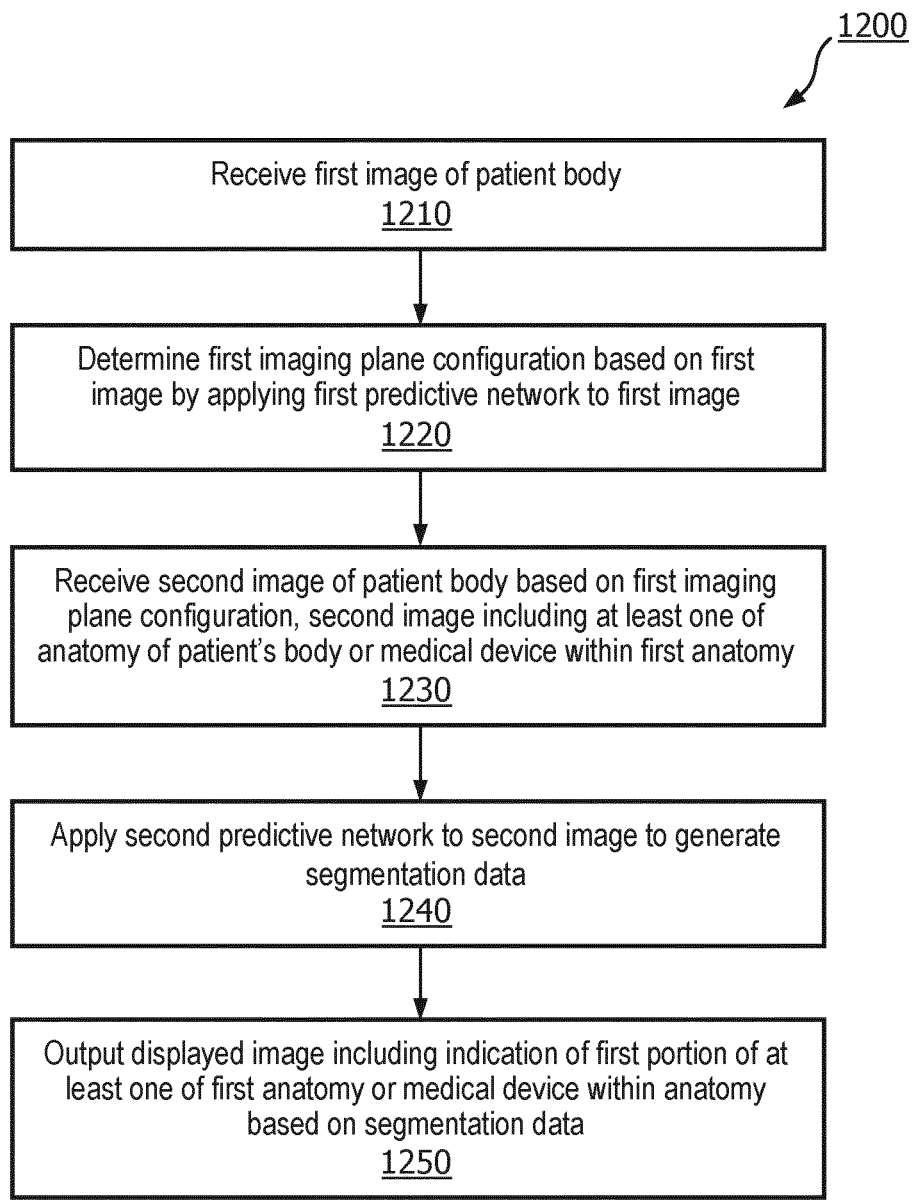
FIG. 12 is a flow diagram of a deep learning-based ultrasound imaging method, according to aspects of the present disclosure.

FIG. 12 is a flow diagram of a deep learning-based ultrasound imaging method 1200, according to aspects of the present disclosure. The method 1200 is implemented by the system 100, for example, by a processor circuit such as the processor circuit 1100, and/or other suitable component such as the probe 110 or 240, the processing component 116, the host 130, and/or the processing component 134. In some examples, the system 100 can include computer-readable medium having program code recorded thereon, the program code comprising code for causing the system 100 to execute the steps of the method 1200. The method 1200 may employ similar mechanisms as in the schemes 200, 300, 400, 500, 600, 700, and/or 1000 described above with respect to FIGS. 2, 3, 4, 5, 6, 7, and/or 10, respectively, and the configurations 800 and/or 900 described above with respect to FIGS. 8 and/or 9, respectively. As illustrated, the method 1200 includes a number of enumerated steps, but embodiments of the method 1200 may include additional steps before, after, and in between the enumerated steps. In some embodiments, one or more of the enumerated steps may be omitted or performed in a different order.

At step 1210, the method 1200 includes receiving, at a processor circuit (e.g., the processing components 134 and 1100) in communication with an ultrasound transducer array (e.g., the array 112), a first image (e.g., the images 202, 402, 502, 602, 604, 702, and/or 1002) of a patient body (e.g., the object 105) from the ultrasound transducer array.

At step 1220, the method 1200 includes determining a first imaging plane configuration (e.g., the imaging plane P1 of FIG. 3) based on the first image by applying a first predictive network (e.g., a deep learning network 810 at the device recognition component 212) associated with image identification to the first image, for example, as shown in the schemes 400 and/or 500.

At step 1230, the method 1200 includes receiving, from the ultrasound transducer array, a second image (e.g., the image 604) based on the first imaging configuration. For instance, the second image is received based at least in part on the first imaging plane configuration. The second image includes an imaging view of at least one of an anatomy of the patient body or a medical device within the anatomy. The medical device may be substantially similar to the medical device 108, 422, 522, 722, and/or 1022). In some examples, the medical device may include at least one of a needle, a guidewire, a catheter, a guided catheter, a therapy device, an interventional device, or a diagnostic device.

At step 1240, the method 1200 includes applying a second predictive network (e.g., e.g., a deep learning network 910 at the device segmentation and tip localization component 216) associated with image segmentation to the second image to generate segmentation data, for example, as shown in the scheme 700.

At step 1250, the method 1200 includes outputting, to a display (e.g., the display 132) in communication with the processor circuit, a displayed image (e.g., the image 604 and 704 of FIG. 7) including an indication of a first portion of the at least one of the anatomy or the medical device based at least in part on the segmentation data. The indication may be similar to the indicators 730, 732, and/or 734 shown in FIG. 7. In an example, the first portion may be a tip (e.g., the tip 724) of the medical device. In an example, the first portion may be a moving portion of the patient's heart.

In an embodiment, the processor circuit further receives, from the ultrasound transducer array, a third image (e.g., the image 602) of the patient body based on the first imaging plane configuration. The processor circuit further determines a second imaging plane configuration (e.g., the imaging plane configuration P2 of FIG. 3) based on the third image (e.g., the image 602). In some instances, the second image is further received based on the second imaging plane configuration.

In an embodiment, the first imaging plane configuration includes a first parameter associated with a first beam steering angle, and the second imaging plane configuration includes a second parameter associated with a second beam steering angle less than the first beam steering angle.

In other words, the first imaging plane configuration includes a first parameter associated with a first imaging resolution and the second imaging plane configuration includes a second parameter associated with a second imaging resolution higher than the first imaging resolution.

In an embodiment, the processor circuit determines the second imaging plane configuration by applying a third predictive network (e.g., a deep learning network 810 at the device tracking component 214) associated with image identification to the third image to generate a second imaging plane configuration, for example, as shown in the scheme 600.

In an embodiment, the processor circuit receives, from the ultrasound transducer array, a sequence of images of the patient body, where the sequence of images includes the first image and each image is received based on a different imaging plane configuration. The processor circuit determines the first imaging plane configuration by applying the first predictive network to each image of the sequence of images to generate a confidence level associated with a presence of the at least one of the anatomy or the medical device in the image and select the first imaging plane configuration based on the confidence level, for example, as shown in the scheme 600.

In an embodiment, the processor circuit determines determining a third imaging plane configuration based on the segmentation data. The third imaging plane configuration may include a parameter associated with at least one of beam steering angle (e.g., as shown in the scheme 1000), a signal gain, or an imaging depth of focus, where the displayed image is further based on the third imaging plane configuration.

Aspects of the present disclosure can provide several benefits. For example, the use of a 3D imaging probe to acquire 2D images, X-plane images, and/or multiplanar images provide the flexibility in acquiring any imaging plane within a volumetric FOV. The performing of device search and/or localization from a coarse resolution scale to a fine resolution scale can reduce the amount of view-finding time. The use of a series of prediction networks in a pipeline configuration for the device search and localization, where the output of one prediction network is used to initialize (e.g., based on image cropping) a next prediction network can reduce the number of iterations required for the closed-loop, and thus may further reduce the view-finding time. The use of a closed-loop form with electronic steering allows for autonomous optimal view finding, providing clinicians with assistance in the most challenging and/or time-consuming task of optimal view-finding in a clinical procedure.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system comprising:
   a processor circuit in communication with an ultrasound transducer array, the processor circuit configured to:
      receive, from the ultrasound transducer array, a first image of a patient body based on a first imaging plane configuration;
      apply a series of predictive networks configured to:
         determine, with a first predictive network associated with image identification, if the first image includes an imaging view of at least one of an anatomy of the patient body or a medical device within the anatomy, wherein the processor circuit applied the first predictive network to the first image;
         determine, with a second predictive network associated with image identification, a second imaging plane configuration different than the first imaging plane configuration, in response to the determination that the first image does not include the imaging view;
      transmit an instruction for the ultrasound transducer array to change from the first imaging plane configuration to the second imaging plane configuration, wherein the instruction is based on an output of the second predictive network;
      receive, from the ultrasound transducer array, a second image of the patient body based on the second imaging plane configuration, wherein the second image includes the imaging view; and
      generate, with a third predictive network associated with image segmentation, segmentation data using the second image, wherein the processor circuit applies the third predictive network to the second image,
   wherein the processor circuit is further configured to output, to a display in communication with the processor circuit, a displayed image including an indication of the at least one of the anatomy or the medical device based on the segmentation data.

2. The system of claim 1, wherein the processor circuit is configured to:
   receive, from the ultrasound transducer array, a third image of the patient body based on the first imaging plane configuration; and
   apply the second predictive network to the third image to determine the second imaging plane configuration.

3. The system of claim 1,
   wherein the first imaging plane configuration includes a first parameter associated with a first beam steering angle, and
   wherein the second imaging plane configuration includes a second parameter associated with a second beam steering angle less than the first beam steering angle.

4. The system of claim 1,
   wherein the first imaging plane configuration includes a first parameter associated with a first imaging resolution, and
   wherein the second imaging plane configuration includes a second parameter associated with a second imaging resolution higher than the first imaging resolution.

5. The system of claim 1, wherein:
the first predictive network includes a convolutional encoder trained to identify the at least one of the anatomy or the medical device based on a first spatial resolution; and
the second predictive network includes a convolutional encoder trained to determine a distance metric associated with an in-plane imaging view of the at least one of the anatomy or the medical device at a second spatial resolution finer than the first spatial resolution.

6. The system of claim 1, wherein:
the first predictive network includes a convolutional encoder trained to identify the at least one of the anatomy or the medical device based on a first image resolution; and
the second predictive network includes a convolutional encoder trained to determine a distance associated with an in-plane imaging view of the at least one of the anatomy or the medical device based on a second image resolution higher than the first image resolution.

7. The system of claim 1, wherein the processor circuit is configured to:
receive, from the ultrasound transducer array, a sequence of images of the patient body, the sequence of images including the first image, and wherein each image of the sequence of images is based on a different imaging plane configuration;
apply the first predictive network to each image of the sequence of images to generate a confidence level associated with a presence of the at least one of the anatomy or the medical device in the image; and
determine if the first image includes the imaging view based on the confidence level.

8. The system of claim 7, wherein the sequence of images includes at least a short-axis image and a long axis-image.

9. The system of claim 1, wherein:
the processor circuit is further configured to determine a third imaging plane configuration based on the segmentation data, the third imaging plane configuration includes a parameter associated with at least one of beam steering angle, a signal gain, or an imaging depth of focus; and
the displayed image is based on the third imaging plane configuration.

10. The system of claim 1, wherein the second image includes the medical device comprising at least one of a needle, a guidewire, a catheter, or a guide catheter.

11. The system of claim 1, wherein the ultrasound transducer array is a two-dimensional (2D) ultrasound transducer array.

12. The system of claim 1,
further comprising an electronic steering controller in communication with the ultrasound transducer array and the processor circuit,
wherein the processor circuit is configured to transmit the instruction to the electronic steering controller.

13. A method of ultrasound imaging, comprising:
receiving, at a processor circuit in communication with an ultrasound transducer array, a first image of a patient body based on a first imaging plane configuration;
applying, with the processor circuit, a series of predictive networks, wherein applying the series of predictive networks comprises:
determining, with a first predictive network associated with image identification, if the first image includes an imaging view of at least one of an anatomy of the patient body or a medical device within the anatomy, wherein the processor circuit applies the first predictive network to the first image; and
determining, with a second predictive network associated with image identification, a second imaging plane configuration different than the first imaging plane configuration, in response to the determination that the first image does not include the imaging view;
transmitting, with the processor circuit, an instruction for the ultrasound transducer array to change from the first imaging plane configuration to the second imaging plane configuration, wherein the instruction is based on an output of the second predictive network;
receiving, from the ultrasound transducer array, a second image of the patient body based on the second imaging plane configuration, wherein the second image includes the imaging view; and
generating, with a third predictive network associated with image segmentation, segmentation data using the second image, wherein the processor circuit applies the third predictive network to the second image, and
wherein the method further comprises outputting, to a display in communication with the processor circuit, a displayed image including an indication of the at least one of the anatomy or the medical device based on the segmentation data.

14. The method of claim 13,
further comprising receiving, from the ultrasound transducer array, a third image of the patient body based on the first imaging plane configuration; and
wherein the processor circuit applies the second predictive network to the third image to determine the second imaging plane configuration.

15. The method of claim 13,
wherein the first imaging plane configuration includes a first parameter associated with a first beam steering angle, and
wherein the second imaging plane configuration includes a second parameter associated with a second beam steering angle less than the first beam steering angle.

16. The method of claim 13,
wherein the first imaging plane configuration includes a first parameter associated with a first imaging resolution, and
wherein the second imaging plane configuration includes a second parameter associated with a second imaging resolution higher than the first imaging resolution.

17. The method of claim 13, further comprising:
receiving, from the ultrasound transducer array, a sequence of images of the patient body, the sequence of images including the first image, and wherein each image of the sequence of images is based on a different imaging plane configuration;
applying the first predictive network to each image of the sequence of images to generate a confidence level associated with a presence of the at least one of the anatomy or the medical device in the image; and
determining if the first image includes the imaging view based on the confidence level.

18. The method of claim 13,
further comprising determining a third imaging plane configuration based on the segmentation data, the third imaging plane configuration includes a parameter associated with at least one of beam steering angle, a signal gain, or an imaging depth of field, wherein the displayed image is based on the third imaging plane configuration.

* * * * *